(12) United States Patent
Cheng et al.

(10) Patent No.: US 11,001,813 B2
(45) Date of Patent: May 11, 2021

(54) METHOD FOR PURIFICATING AND CRYSTALLIZATING LPOR PROTEIN AND USE THEREOF

(71) Applicant: Zhejiang Shance HeQiShi Bio-Sci & Tech. Co., Ltd., Jiaxing (CN)

(72) Inventors: Qi Cheng, Zhejiang (CN); Wenli Sun, Zhejiang (CN)

(73) Assignee: Zhejiang Shance HeQiShi Bio-Sci&Tech.Co., Ltd., Jiaxing (CN)

( * ) Notice: Subject to any disclaimer, the term of this patent is extended or adjusted under 35 U.S.C. 154(b) by 0 days.

(21) Appl. No.: 16/993,847

(22) Filed: Aug. 14, 2020

(65) Prior Publication Data

US 2020/0385691 A1    Dec. 10, 2020

Related U.S. Application Data

(63) Continuation of application No. PCT/CN2019/103936, filed on Sep. 2, 2019.

(30) Foreign Application Priority Data

| Sep. 3, 2018 | (CN) | 201811020621.0 |
| Sep. 3, 2018 | (CN) | 201811021496.5 |
| Sep. 3, 2018 | (CN) | 201811022544.2 |
| Sep. 3, 2018 | (CN) | 201811022545.7 |
| Sep. 3, 2018 | (CN) | 201811023329.4 |

(51) Int. Cl.
*C12N 9/02* (2006.01)
*C12N 15/70* (2006.01)

(52) U.S. Cl.
CPC ............ *C12N 9/001* (2013.01); *C12N 15/70* (2013.01); *C12Y 103/01033* (2013.01)

(58) Field of Classification Search
None
See application file for complete search history.

(56) References Cited

FOREIGN PATENT DOCUMENTS

| CN | 102121026 A | 7/2011 |
| CN | 103333219 A | 10/2013 |
| CN | 103436591 A | 12/2013 |
| WO | 2007/075253 A2 | 7/2007 |

OTHER PUBLICATIONS

International Search Report for International Application No. PCT/CN2019/103963 filed Sep. 2, 2019, 5 pages.
McPherson. A. "Crystallization of Proteins from Polyethylene Glycol" The Journal of Biological Chemistry, vol. 251, No. (20), Oct. 25, 1976 (Oct. 25, 1976), pp. 6300-6303.

*Primary Examiner* — Suzanne M Noakes
*Assistant Examiner* — Jae W Lee
(74) *Attorney, Agent, or Firm* — Thomas Horstemeyer, LLP

(57) ABSTRACT

Provided are a method for purifying and crystallizing the LPOR protein, wherein a protein and a crystal with complete structure can be obtained. Also provided are the three-dimensional spatial structure and binding site of the LPOR protein, and the use of the protein.

16 Claims, 16 Drawing Sheets
Specification includes a Sequence Listing.

pEHISTEV1LPOR pEBMSCHISLPOR pBADHISTEV1LPOR pEBSRCTEVC10HISLPOR

M    LPOR atggaacaaccgatgaaacccacggtgatcatcaccggagcctcctccggggtgggattatacggagctaaagctttaattgacaaaggttggc
acgtgattatggcctgccgcaatttggataaaacccagaaagtagccgatgaattgggttttcccaaggattcctacaccatcatcaaattggattt
gggctatctggacagtgtgcgccgctttgtcgcccagtttcgggaattgggtcgtcccctcaaagctctggtttgtaatgcggcggtttattttccttt
gctggacgaacccctctggtcagcggatgactatgaactttctgtggcgaccaaccacctggggcacttttgctttgcaatctgttgttggaagatt
taaaagcctgtcccgatgcagataagcgtttaatcattttgggcactgttacggccaacagcaaagaactaggggggtaaaattcccatccccgcc
ccgccggatttgggcaactttgaagggtttgaagcgggctttaagaaacccattgccatgattaataacaaaaaattcaaatcgggcaaagcgtat
aaagatagtaagctctgcaatatgctcaccaccagggagttgcaccgtcgcttccaccaagaaacgggcatcgttttttaattctctctatccgggct
gtgtagccgatactcccctattccgcaatcactattccttgttccgcaccattttccctggttccagaaaaacgttaccaaaggctatgtcagccaa
gaattggcaggggaacgggtggccatggtggtggccgatgacaaatttaaggattctggggtgcattggagctggggcaaccgtcaacaagc
gggccgggaagcctttgtgcaggaactttcggaacagggaagcgatgcccaaaaagctcagcgcatgtgggatctaagcgaaaagttagtgg
gtctggtttagctcgag (SEQ ID NO: 3)

FIG. 22 atggaacaaccgatgaaacccacggtgatcatcaccggagcctcctccggggtgggattatacggagctaaagctttaattgacaaaggttggc
acgtgattatggcctgccgcaatttggataaaacccagaaagtagccgatgaattgggttttcccaaggattcctacaccatcatcaaattggattt
gggctatctggacagtgtgcgccgctttgtcgcccagtttcgggaattgggtcgtcccctcaaagctctggtttgtaatgcggcggtttattttccttt
gctggacgaacccctctggtcagcggatgactatgaactttctgtggcgaccaaccacctggggcacttttgctttgcaatctgttgttggaagatt
taaaagcctgtcccgatgcagataagcgtttaatcattttgggcactgttacggccaacagcaaagaactaggggggtaaaattcccatccccgcc
ccgccggatttgggcaactttgaagggtttgaagcgggctttaagaaacccattgccatgattaataacaaaaaattcaaatcgggcaaagcgtat
aaagatagtaagctctgcaatatgctcaccaccagggagttgcaccgtcgcttccaccaagaaacgggcatcgttttttaattctctctatccgggct
gtgtagccgatactcccctattccgcaatcactattccttgttccgcaccattttccctggttccagaaaaacgttaccaaaggctatgtcagccaa
gaattggcaggggaacgggtggccatggtggtggccgatgacaaatttaaggattctggggtgcattggagctggggcaaccgtcaacaagc
gggccgggaagcctttgtgcaggaactttcggaacagggaagcgatgcccaaaaagctcagcgcatgtgggatctaagcgaaaagttagtgg
gtctggtttag (SEQ ID NO: 4)

FIG. 23

LPOR-6803 amino acid sequence
Meqpmkptviitgassgvglygakalidkgwhvimacrnldktqkvadelgfpkdsytiikldlgyldsvrrfvaqfrelgrplkalvcna
avyfplldeplwsaddyelsvatnhlghfllcnlllledlkacpdadkrliilgtvtanskelggkipipappdlgnfegfeagfkkpiaminnk
kfksgkaykdsklcnmlttrelhrrfhqetgivfnslypgcvadtplfrnhyslfrtifpwfqknvtkgyvsqelagervamvvaddkfkds gvhwswgnrqqagreafvqelseqgsdaqkaqrmwdlseklvglv* (SEQ ID NO: 13)

FIG. 24

The original LPOR gene sequence:
ATGAGTGATCAGCCACGCCCAACGGTCATTATTACGGGTGCATCCTCTGGAGTCGGATTG
TATGCTACCAAGGCCTTAGCCAATCGGGGCTGGCACGTTATAATGGCCTGCCGCAATCTT
GAAAAAGCAGAGCAAGCCGCCAAAAACTTGCAGATTCCGCCGGAGGCCTACACGATTT
TGCACTTGGACTTGTCCTCCTTGGCCAGTGTGCGCGGCTTTGTTGAATCATTTCGGGCAT
TGAATCGCCCCTTGCGTGCCCTTGTCTGCAATGCCGCTGTCTATTATCCCCTGCTCAAGG
AACCTATCTACAGTGTGGATGGCTATGAAATCACTGTGGCCACCAACCATTTGGGGCATT
TTCTTTTGATCAACCTGCTGCTAGAAGACTTGAAAAATTCTCCCGAAAGCGATAAGCGC
TTGGTGATTCTCGGCACAGTGACAGCCAACCGCAAAGAACTCGGCGGTAAAATTCCCAT
TCCTGCTCCCCTGATTTGGGCAACCTCGAAGGCTTTGAAAAAGGCTTCAAGAAGCCGA
TTGCCATGATTAACGGTAAGCCCTTCAAGTCGGGCAAGGCCTACAAAGACAGCAAGCTC
TGCAATATGCTGACGGCACGGGAACTGCATCGCCGCTTTCACGAGAGCACCGGAATTGT
TTTTAATTCCCTTTACCCCGGTTGTGTGGCCGACACACCCCTGTTTCGCCACCACTTCCC
CCTGTTTCAGAAACTCTTCCCCCTCTTCCAGAAAAAGATTACTGGGGCTATGTCAGCC
AAGAACTGGCGGGTGAGCGCGTCGCGATGGTGGTCGCAGACCCAGAGTTTCGCCAGTC
GGGGGTCCACTGGAGCTGGGGTAATCGCCAAAAAGAAGGCCGCAAAGCCTTTGTCCAA
GAACTATCGGCAGAGGCAAGTGATGAGCAAAAAGCCCGCCGTCTTTGGGAGCTGAGTG
AAAAACTGGTGGGATTGGCC(SEQ ID NO: 10)

FIG. 25

The nucleic acid sequence after mutation of LPOR:
ATGAGTGATCAGCCACGCCCAACGGTCATTATTACGGCTGCATCCTCTGTAGTCGTGTTG
TATGCTACCAAGGCCTTAGCCAATCGGGGCTTGCACGTTATAATGGCCAGCCGCAATCTT
GAAAAAGCAGAGCAAGCCGCCAAAAACTTGCAGATTCCGCCGGAGGCCTACACGATTT
TGCACTTGGACTTGTCCTCCTTGGCCAGTGTGCGCGGCTTTGTTGAATCATTTCGGGCAT
TGAATCGCCCCTTGCGTGCCCTTGTCTACAATGCCGCTGTCTATTATCCCCTGCTCAAGG
AACCTATCTACAGTGTGGATGGCTATGAAATCACTGTGGCCACCAACCATTTGGGGCATT
TTCTTTTGATCAACCTGCTGCTAGAAGACTTGAAAAATTCTCCCGAAAGCGATAAGCGC
TTGGTGATTCTCGGCACAGTGACAGCCAACCGCAAAGAACTCGGCGGTAAAATTCCCAT
TCCTGCTCCCCTGATTTGGGCAACCTCGAAGGCTTTGAAAAAGGCTTCAAGAAGCCGA
TTGCCATGATTAACGGTAAGCCCTTCAAGTCGGGCAAGGCCTTCAAAGACAGCATGCTC
AGCAATATGCTGACGGCACGGGAACTGCATCGCCGCTTTCACGAGAGCACCGGAATTGT
TTTTAATTCCCTTTACCCCGGTGGTGTGGCCGACACACCCCTGTTTCGCCACCACTTCCC
CCTGTTTCAGAAACTCTTCCCCGACTTCCAGAAAAAGATTACTGGGGCTATGTCAGCC
AAGAACTGGCGGGTGAGCGCGTCGCGATGGTGGTCGCAGACCCAGAGTTTCGCCAGTC
GGGGGTCCACTGGACCTGGGGTAATCGCCAAAAAGAAGGCCGCAAAGCCTTTGTCCAA
GAACTATCGGCAGAGGCAAGTGATGAGCAAAAAGCCCGCCGTCTTTGGGAGCTGAGTG
AAAAACTGGTGGGATTGGCC (SEQ ID NO: 7)
Y193F N    5' GCAAGGCCTTCAAAGACAGCATGCTCAGCAATATGCTG 3'(SEQ ID NO: 8)
Y193F C    5' GTCTTTGAAGGCCTTGCCCGACTTGAAGGGCTTACCG 3'(SEQ ID NO: 9)

FIG. 26

The amino acid sequence of the original LPOR:
MSDQPRPTVIITGASSGVGLYATKALANRGWHVIMACRNLEKAEQAAKNLQIPPEAYTILHL
DLSSLASVRGFVESFRALNRPLRALVCNAAVYYPLLKEPIYSVDGYEITVATNHLGHFLLINL
LLEDLKNSPESDKRLVILGTVTANRKELGGKIPIPAPPDLGNLEGFEKGFKKPIAMINGKPFK
SGKAYKDSKLCNMLTARELHRRFHESTGIVFNSLYPGCVADTPLFRHHFPLFQKLFPLFQKK
ITGGYVSQELAGERVAMVVADPEFRQSGVHWSWGNRQKEGRKAFVQELSAEASDEQKAR
RLWELSEKLVGLA (SEQ ID NO: 11)

The amino acid sequence of the mutation LPOR:
MSDQPRPTVIITGASSGVGLYATKALANRGWHVIMACRNLEKAEQAAKNLQIPPEAYTILHL
DLSSLASVRGFVESFRALNRPLRALVCNAAVYYPLLKEPIYSVDGYEITVATNHLGHFLLINL
LLEDLKNSPESDKRLVILGTVTANRKELGGKIPIPAPPDLGNLEGFEKGFKKPIAMINGKPFK
SGKAFKDSKLCNMLTARELHRRFHESTGIVFNSLYPGCVADTPLFRHHFPLFQKLFPLFQKKI
TGGYVSQELAGERVAMVVADPEFRQSGVHWSWGNRQKEGRKAFVQELSAEASDEQKARR
LWELSEKLVGLA(SEQ ID NO: 12)

FIG. 27

METHOD FOR PURIFICATING AND CRYSTALLIZATING LPOR PROTEIN AND USE THEREOF

RELATED APPLICATIONS

This application is a continuation application of International Application Serial No. PCT/CN2019/103936, filed Sep. 2, 2019. International Application Serial No. PCT/CN2019/103936 claims the benefit of Chinese Patent Application Nos. 201811020621.0, 201811021496.5, 201811022544.2, 201811022545.7, and 201811023329.4, filed on Sep. 3, 2018. Each of these applications is incorporated herein by reference in its entirety.

FIELD OF THE INVENTION

The invention relates to a technical field of protein engineering, in particular to a method for expression, purification and crystallization of an LPOR protein, and the use of the protein.

BACKGROUND OF THE INVENTION

LPOR (light-dependent protochlorophyllide oxidoreductase) is a key enzyme for chlorophyll synthesis in cyanobacteria, algae and multicellular plants. In the photosynthesis pathway, organisms catalyze the reduction of prochlorophyllPchlide by two different reductases: one is light-dependent NADPH (protochlorophyllideoxidoreductase), the other is light-dependent Pchlide oxidation Reductase DPOR (light-independent protochlorophyllide oxidoreductase). LPOR or DPOR, as protochlorophyllate lipid reduction catalytic enzymes, are the key enzymes of chlorophyll synthesis in photosynthetic nutritional organisms. Both of these enzymes are widely present in phototrophic organisms. However, DPOR and LPOR are in molecular structure, subunit composition, genome coding and catalytic reaction mechanisms are completely different. DPOR is encoded by the chloroplast genome and consists of three protein subunits; LPOR is encoded by the nuclear genome; DPOR and LPOR have similar functions and can catalyze the reduction of the Pchlide D ring double bond. Among them, anaerobic photosynthetic bacteria only have DPOR; gymnosperms, algae, cyanobacteria and photosynthetic bacteria have DPOR and LPOR; angiosperms only have LPOR.

In the past ten years, research on the regulation, function and catalytic mechanism of LPOR has made great progress, but since the veil of the three-dimensional structure of LPOR has not been revealed, it is necessary to thoroughly clarify and determine the catalytic mechanism of LPOR or to change it. Engineering has formed an insurmountable harder. For many years, scientists have tried to provide clues to biochemists by means of computer simulation. However, these are only speculations. The difficulty in analyzing the structure of the LPOR protein is the purification and crystallization process.

Protein purification technology is widely used. Based on the structure and function of proteins, understanding of life phenomena at the molecular level has become the main direction of modern biological development. To study proteins, we must first obtain highly purified and biologically active target substances. The preparation of proteins involves physical, chemical and biological knowledge, but the basic principle is nothing more than two aspects: one is to use the difference in the distribution ratios of several components in the mixture to distribute them to two or in several phases, such as salting out, organic solvent extraction, chromatography and crystallization, etc.; Second, the mixture is placed in a single phase, and the components are distributed in the same area through the action of the physical force field to achieve the purpose of separation, such as electrophoresis, ultracentrifugation, ultrafiltration, etc. In the uses of all these methods, care must be taken to preserve the integrity of biological macromolecules, and to prevent the loss of biological activity of the substances mentioned by acid, alkali, high temperature, and severe mechanical effects. Although the technology of protein purification is very mature, it is still a difficult point in the research of protein purification for some extremely unstable photosensitivity proteins.

SUMMARY OF THE INVENTION

In view of this, the present invention provides a method for expression and purification of LPOR protein, which makes the LPOR protein have high activity, provides experimental techniques for the expression and purification of other light-sensitive superfast proteins, and lays the foundation for the structural analysis of light-sensitive superfast proteins. At the same time, it has laid the foundation for thoroughly elucidating and determining the catalytic mechanism of light-sensitive superspeed proteins or engineering them. In order to achieve the above objective, the present invention provides the following technical solutions: A method for expressing an LPOR protein, including the following steps:

(1) Screening the DNA sequence of the LPOR gene and designing two primers based on the LPOR protein nucleotide sequence NC_004113 published in GenBank, and adding BspHI/BamHI restriction sites at both ends of the primer. The DNA sequence of the LPOR gene selected from the NC_004113 sequence is SEQ ID NO: 3; and select a prokaryotic expression vector; wherein the primer sequence is:

```
LPORN:
                                SEQ: ID NO: 1
TCATGAATGAGTGATCAGCCACG;;

LPORC:
                                SEQ ID NO: 2
GGATCCGGCCAATCCCACCAGTTTTTC;;
```

(2) Performing PCR amplification on the DNA sequence of the LPOR gene obtained in step (1);

(3) Double digestion;

Purify the PCR product obtained in step (2) with BspHI/BamHI, and cut the prokaryotic expression vector with BspHI/BamHI, and recover the digested PCR product and large fragment of prokaryotic expression vector;

(4) construction of LPOR expression vector;

the enzyme-digested PCR product and the large fragment of the prokaryotic expression vector are obtained in step (3), mixing and ligating at a ratio of 10:1-5:5, and the Obtained ligated product is transferred into competent cells to obtain an LPOR expression vector;

(5) screening of LPOR expression vector:

The LPOR expression vector obtained in step (3) is picked and cultured on a screening plate culture medium. Long positive monoclonals are picked, plasmids are extracted, and the enzyme digestion is verified to confirm that the sequencing is incorrect. The LPOR expression vector with the confirmed sequencing is stored for future use.

(6) LPOR protein expression

The LPOR expression vector constructed in step (5) is transferred into a prokaryotic expression strain, cultured at 25-37° C. for 24-48 Ii, and an inducer was added to express the LPOR protein.

Wherein, the PCR amplification conditions in step (2) of the present invention are: 95° C. for 4 min, 25 cycles of cyclic amplification at 95° C. for 40 sec, 55° C. for 30 sec, and 72° C. for 1 min. In the step (6) of the present invention, a pull-down detection result is performed according to the expression of the LPOR protein. The expression is high and the pull-down results are small in a band, and the band can be used for the purification of the LPOR protein further.

In one embodiment, the prokaryotic expression vector in step (I) is one of pEHISTEV, pBADHISTEV1, pEBMSCHIS, or pEBSRCTEVC10HIS.

In one embodiment, the competent cell in step (4) is *E. coli* DH5α.

In one embodiment, the screening plate medium in step (5) is a kanamycin or ampicillin-resistant medium containing 50-150 mg/L.

In one embodiment, the prokaryotic expression strain in step (6) is *E. coli* C43, *E. coli* BL21 or 194 strain.

In one embodiment, the inducer in step (6) is 0.1-1.0 mM IPTG or L-Arabinose with a mass concentration of 0.01-0.05%.

In another aspect, the present invention provides a method for purifying an LPOR protein, including the following steps:

(1) His-tag affinity chromatography

Pretreatment steps of affinity chromatography: Centrifuging the bacterial solution induced by the inducer, collecting the bacterial cells and washing them with a washing solution, which are rinsed with an equilibrium solution, and the cells are re-suspended with 35 mL/g of the equilibrium solution. The bacterial solution treated as above was broken by ultrasonically, the supernatant was taken off after centrifugation, and then filtered by vacuum, and then His-tag affinity chromatography was performed;

(2) Protein concentration

Adding the protein obtained in step (1) to the ultrafiltration cup, 3000-5000 rpm, and centrifuged until the required volume is reached, stop the centrifugation, and determine the protein concentration;

(3) Gel filtration

The concentrated protein obtained in step (2) is added to 0.5 uM NADPH coenzyme, and then subjected to gel filtration chromatography to collect a protein sample, and the protein sample is subjected to sds-page analysis to obtain a protein sample of a single target band, and then using the ultra-filtration cup concentrates the protein sample to a concentration of 10-15 mg/ml.

Preferably, the method for centrifuging the bacterial solution in step (1) is 3000-5000 rpm for 20 min.

Preferably, the washing solution in step) is a 0.1 mM PBS liquid.

Preferably, the method of step (1) sonicating the bacterial liquid is 200 W power, ½ probe, crushing for 30 s, and intermittently for 30 S.

Preferably, the centrifugation method after the ultrasonication of the bacterial solution in step (1) is 16000-19000 rpm, and the centrifugation is performed for 20 minutes.

Preferably, the His-tag affinity chromatography purification method includes equilibration, loading, washing, elution, and storage. The specific operation method is:

Equilibration: Equilibrate the pre-packed column with the equilibration solution (loading buffer), turn on the UV detector, adjust the wavelength to 280 nm, the sensitivity is 100%, and preheat to make the liquid flow down at a uniform speed (3 mL min). The amount of light keeps the absorption value stable at 100. At this time, it is full. After the absorption value is stable, adjust the sensitivity to 0.5 A/0.2 A to keep the absorption value stable at 0. This is the baseline adjustment.

Loading: Slowly add the sample processed in advance to the column to avoid the generation of air bubbles. Keep the flow rate as low as possible (1 mL/min). When the absorbance value is greater than 20, use a 50 ml centrifuge tube to connect the protein solution. The flow-through is called, and the protein in the flow-through should be a bacterial protein that is not bound to the gel.

Washing: Slowly add binding buffer along the wall, turn on the switch, and take more than 10 column volumes of binding buffer. The flow rate is 3 mL/min to restore the absorbance to or near baseline.

Elution: First select 50 mM imidazole as the flow washing concentration, mainly eluting the bacterial protein that is not specifically hound in the gel, and 100-500 mM imidazole as the elution concentration, mainly eluting the target protein, and each elution concentration The proteins were detected by SDS electrophoresis.

Storage: After elution, wash the column with 3 times the volume of sterilized water, inject 20% ethanol, so that the gel is fully immersed in ethanol, and store at 4° C. until use.

Washing: Slowly add binding buffer along the wall, turn on the switch, and take more than 10 column volumes of binding buffer. The flow rate is 3 mL/min to restore the absorbance to or near baseline. Elution: First select 50 mM imidazole as the flow washing concentration, mainly eluting the bacterial protein that is not specifically bound in the gel, and 100-500 mM imidazole as the elution concentration, mainly eluting the target protein, and each elution concentration The proteins were detected by SDS electrophoresis. Storage: After elution, wash the column with 3 times the volume of sterilized water, inject 20% ethanol, so that the gel is fully immersed in ethanol, and store at 4° C. until use.

The ultrafiltration cup was rinsed three times with double distilled water, and then double distilled water was added to the ultrafiltration cup, and centrifuged at 3000 rpm for 10 minutes. The filter membrane was thoroughly cleaned, the double distilled water was discarded, and Protein samples.

Preferably, the method for determining the protein concentration in step (2) is nanodrop.

Preferably, the gel chromatography method is as follows: the pre-assembled column is connected to the instrument akta-xpress, and the gel filtration buffer is used to equilibrate 1.5 times the column volume; after the equilibrium is completed, the sample obtained in step (2) is injected. Adjust the flow rate to 1 ml/min, turn on the UV detection system, and collect samples when the protein flows out. After the end, wash the column with 1.5 times the double bed volume of double-distilled water and save it for future use.

Further, in the vacuum filtration in step (1), a 0.45 μm filter membrane is used for filtration.

Further, the ultrafiltration cup in step (2) is a 30 kd ultrafiltration cup.

Further, the gel filtration chromatography in step (3) is a sephadex g-75 gel chromatography column.

It can be known from the above technical scheme that compared with the prior art, the present invention provides a method for the expression and purification of LPOR protein, which has the following technical advantages: The invention provides a method for the expression and purification of LPOR protein, which solves the current photosynthesis the important problem of LPOR protein purification and its high activity has laid the foundation for thoroughly elucidating and determining the catalytic mechanism of LPOR protein or engineering it; and for the further understanding of the structure of light-sensitive super-speed proteins.

In another aspect, the present invention provides a method for protein crystallization of a light-sensitive protein LPOR, the method comprising: providing a purified and concentrated LPOR protein sample, consisting of 18% PEG20000 and 0.1M NaAc, in a crystallization buffer at pH 4.5 Crystallize.

In another aspect, the present invention provides a method for protein crystallization of a light-sensitive protein LPOR, comprising the steps of: providing a purified and concentrated LPOR protein sample, and crystallizing from 50 ul LMB1 A7 and 10 ul additive screen 10 (ZnCl2) to obtain crystals protein.

In some embodiments, the LPOR protein is concentrated through an AmiconUltra-30k ultrafiltration membrane, and the concentration is 30 mg/mL as measured by Nanodrop.

In some embodiments, the LPOR protein is obtained by in vitro expression.

In some embodiments, an expression method of an LPOR protein expressed in vitro includes the following steps:

(1) Screening the DNA sequence of the LPOR gene

Design primers based on the LPOR protein nucleotide sequence NC_004113 published in GenBank, and add BspHI/BamHI restriction sites at both ends of the primer. The DNA sequence of the LPOR gene selected from the NC_004113 sequence is SEQ. ID NO 3 And select a prokaryotic expression vector;

Wherein the primer sequence is

```
LPORN:
                              SEQ ID NO: 1
TCATGAATGAGTGATCAGCCACG;

LPORC:
                              SEQ ID NO: 2
GGATCCGGCCAATCCCACCAGTTTTTC;;
```

(2) Performing PCR amplification on the DNA sequence of the LPOR gene obtained in step (1);

(3) Double digestion

Purify the PCR product obtained in step (2) with BspHI/BamHI, and cut the prokaryotic expression vector with BspHI/BamHI, and recover the digested PCR product and large fragment of prokaryotic expression vector;

(4) Construction of LPOR expression vector The enzyme-digested PCR product obtained in step (3) and the large fragment of the prokaryotic expression vector are mixed and ligated at a ratio of 10:1-5:5, and the obtained ligated product is transferred into competent cells to obtain an LPOR expression vector;

(5) Screening of LPOR expression vector The LPOR expression vector obtained in step (3) is picked and cultured on a screening plate culture medium. Long positive monoclonals are picked, plasmids are extracted, and the enzyme digestion is verified to confirm the sequencing. The LPOR expression vector with the correct sequencing results is stored for later use.

(6) LPOR protein expression: the LPOR expression vector constructed in step (5) was transferred into a prokaryotic expression strain, cultured at 25-37° C. for 24-48 h, and an inducer was added to express the LPOR protein; wherein, the PCR amplification conditions in step (2) of the present invention are: 95° C. for 4 min, 25 cycles of cyclic amplification at 95° C. for 40 sec, 55° C. for 30 sec, and 72° C. for 1 min. In the step (6) of the present invention, a pull-down detection result is performed according to the expression of the LPOR protein. The expression is high and the pull-down results are small, and the band can be used for purification of the LPOR protein. Further, the prokaryotic expression vector in step (1) is one of pEHISTEV, pBADHISTEV1, pEBMSCHIS, or pEBSRCTEVC10HIS. Further, the competent cell in step (4) is $E.$ $coli$ DH5a.

Further, the screening plate medium in step (5) is a kanamycin or ampicillin-resistant medium containing 50-150 mg/L.

Further, the prokaryotic expression strain in step (6) is $E.$ $coli$ C43, $E.$ $coli$ BL21 or 194 strain.

Further, the inducer in step (6) is 0.1-1.0 mM IPTG or L-Arabinose with a mass concentration of 0.01-0.05%.

In some methods, the protein needs to be purified and concentrated after in vitro expression, and the purification method is a Ni-affinity chromatography column.

BRIEF DESCRIPTION OF THE FIGURES

In order to more clearly explain the embodiments of the present invention or the technical solutions in the prior art, the figures used in the description of the embodiments or the prior art will be briefly introduced below. Obviously, the figures in the following description is merely an embodiment of the present invention. For those of ordinary skill in the art, other figures can be obtained according to the provided figures without paying creative labor.

FIG. 22 is a LPOR full-length sequence nucleic acid sequence.

FIG. 23 is the nucleic acid sequence of the LPOR-6803 protein.

FIG. 24 is the amino acid sequence of LPOR-6803.

FIG. 25 is the original LPOR gene sequence.

FIG. 26 shows the nucleic acid sequence after mutation and primers for mutation.

FIG. 27 shows the amino acid sequence of the original LPO and the mutated amino acid sequence

DETAILED DESCRIPTION

In the following, the technical solutions in the embodiments of the present invention will be clearly and completely described with reference to the figures in the embodiments of the present invention. Obviously, the described embodiments are only a part of the embodiments of the present invention, but not all the embodiments. Based on the embodiments of the present invention, all other embodiments obtained by a person of ordinary skill in the art without creative efforts shall fall within the protection scope of the present invention.

Example 1: Expression of LPOR Protein

Primers were designed according to the nucleotide sequence (NC_004113) of the LPOR (*Thermosynechococcus*) protein published in the gene bank. The LPOR full-length gene DNA sequence (SEQ ID NO: 3, FIG. 23) was cloned from *Thermosynechococcus*. For BamHI digestion sites, the prokaryotic expression vector pEHISTEV (purchased from Thermo Fisher) was selected; pEBSRCTEVC10HIS (purchased from Thermo Fisher) was used as the target vector. Among them, pEHISTEV, pBADHISTEV1, pEBMSCHIS, and pEBSRCTEVC10HIS (purchased from Thermo Fisher) as the expression vectors of the LPOR expression vector are shown in FIGS. 1-4.

Among them, the PCR amplification conditions were: 95° C. for 4 min, 25 cycles of cycling at 95° C. for 40 sec, 55° C. for 30 sec, and 72° C. for 1 min. After purification of the PCR product, the expression vector pEHISTEV; pBADHISTEV1, pEBMSCHIS, and pEBSRCTEVC10HIS plasmids were digested with BspHI/BamHI respectively. The digested PCR product and the large fragment of the expression vector were recovered, mixed and ligated at 7:3, and the ligation product was transformed into *E. coli* DH5α. (Purchasing SanboYuanzhi Company), pick positive clones grown on kanamycin (pEHISTEV)/ampicillin (pBADHISTEV1, pEBMSCHIS, pEBSRCTEVC10HIS) resistant plates, take plasmids, and confirm sequencing by confirming correct digestion; The correct LPOR expression vector for sequencing results was stored for future use.

Figure 1:
FIG. 1 is a schematic diagram of an LPOR expression vector using pEHISTEV as an expression vector.
Figure 2:
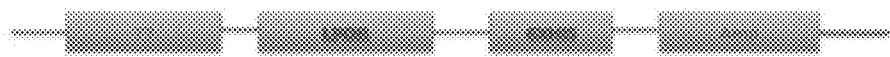
FIG. 2 is a schematic diagram of an LPOR expression vector using pEBMSCHIS as an expression vector.
Figure 3:
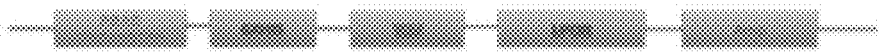
FIG. 3 is a schematic diagram of an LPOR expression vector using pBADHISTEV1 as an expression vector.
Figure 4:
FIG. 4 is a schematic diagram of an LPOR expression vector using pEBSRCTEVC10HIS as an expression vector.
Figure 5:
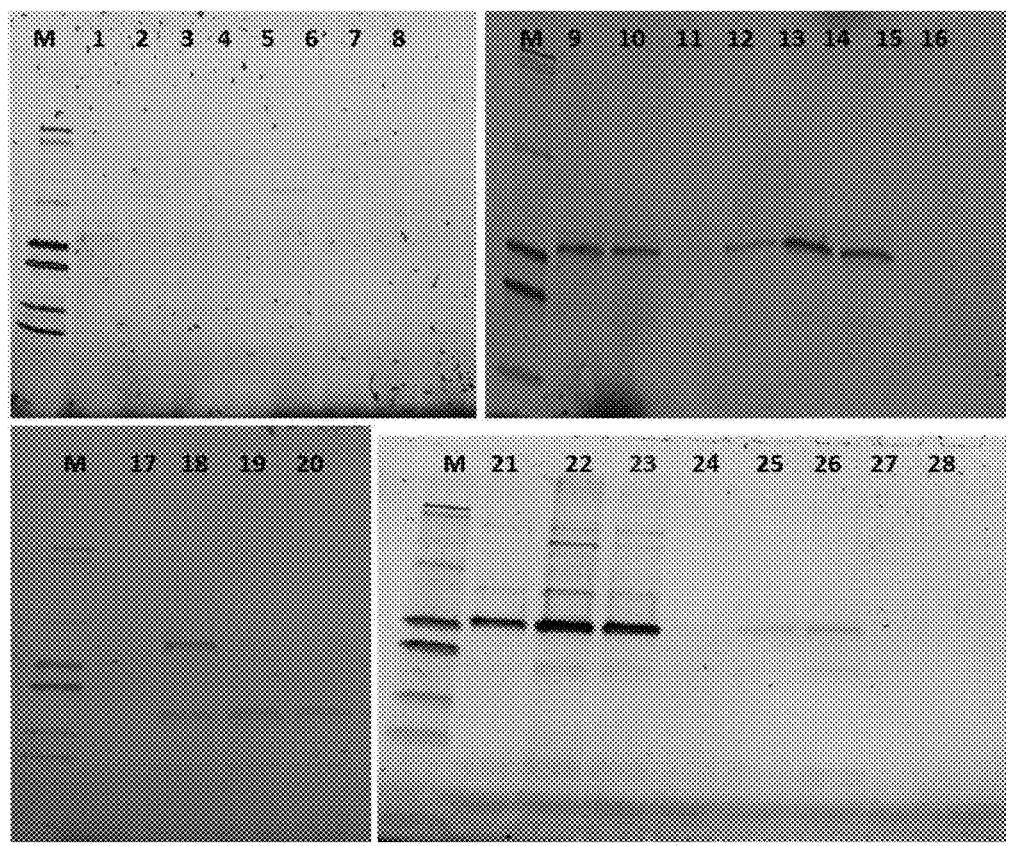
FIG. 5 is a pull-down band diagram under different expression strains, different induction temperatures, and different inducers.

The above constructed prokaryotic expression vectors were transferred into different prokaryotic expression strains *Escherichia coli* C43 (purchased from SanboYuanzhi Company), *E. coli* BL21 (purchased from SanboYuanzhi Company) or pE194 (purchased from SanboYuanzhi Company) with different expressions. The vectors were screened for LPOR protein expression under different expression strains, different induction temperatures, and different inducer (IPTG/L-Arabinose) concentrations, that is, as shown in Table 1 for each group of conditions. LPOR proteins obtained in each group in Table 1 were subjected to a pull-down test to determine the optimal expression conditions. The results are shown in FIG. 5.

TABLE 1

LPOR protein expression under different conditions.

| Serial Number | Carrier | Host strain | Induced temperature | Inducer and concentration |
|---|---|---|---|---|
| 1 | pEHISTEV | C43 | 37 | 0.4 mMIPTG |
| 2 | pEHISTEV | C43 | 37 | 1.0 mMIPTG |
| 3 | pEHISTEV | C43 | 25 | 0.4 mMIPTG |
| 4 | pEHISTEV | C43 | 25 | 1.0 mMIPTG |
| 5 | pEHISTEV | BL21 | 37 | 0.4 mMIPTG |
| 6 | pEHISTEV | BL21 | 37 | 1.0 mMIPTG |
| 7 | pEHISTEV | BL21 | 25 | 0.4 mMIPTG |
| 8 | pEHISTEV | BL21 | 25 | 1.0 mMIPTG |
| 9 | pEBMSCHIS | C43 | 37 | 0.4 mMIPTG |
| 10 | pEBMSCHIS | C43 | 37 | 1.0 mMIPTG |
| 11 | pEBMSCHIS | C43 | 25 | 0.4 mMIPTG |
| 12 | pEBMSCHIS | C43 | 25 | 0.4 mMIPTG |
| 13 | pEBMSCHIS | BL21 | 37 | 0.4 mMIPTG |
| 14 | pEBMSCHIS | BL21 | 37 | 1.0 mMIPTG |
| 15 | pEBMSCHIS | BL21 | 25 | 0.4 mMIPTG |
| 16 | pEBMSCHIS | BL21 | 25 | 0.4 mMIPTG |
| 17 | pBADHISTEV1 | 194 | 37 | 0.02% L-Arabinose |
| 18 | pBADHISTEV1 | 194 | 37 | 0.04% L-Arabinose |
| 19 | pBADHISTEV1 | 194 | 25 | 0.02% L-Arabinose |
| 20 | pBADHISTEV1 | 194 | 25 | 0.04% L-Arabinose |
| 21 | pEBSRCTEVC10HIS | C43 | 37 | 0.4 mMIPTG |
| 22 | pEBSRCTEVC10HIS | C43 | 37 | 1.0 mMIPTG |
| 23 | pEBSRCTEVC10HIS | C43 | 25 | 0.4 mMIPTG |
| 24 | pEBSRCTEVC10HIS | C43 | 25 | 1.0 mMIPTG |
| 25 | pEBSRCTEVC10HIS | BL21 | 37 | 0.4 mMIPTG |
| 26 | pEBSRCTEVC10HIS | BL21 | 37 | 1.0 mMIPTG |
| 27 | pEBSRCTEVC10HIS | BL21 | 25 | 0.4 mMIPTG |
| 28 | pEBSRCTEVC10HIS | BL21 | 25 | 1.0 mMIPTG |

FIG. 5 shows the measurement results according to the numbers in Table 1. It can be seen that the number of miscellaneous bands under the condition of number 21 is the highest, and the content of the target protein is also relatively high, while other carriers, other temperatures, and inducers have some banding. Some are relatively low in content, and some have no protein expression. Therefore, according to FIG. 5, it can be known that the optimal expression conditions are pEBSRCTEVC10HIS-C43-37° C.-0.4 mM IPTG, and the amount of expression is high and the amount of pulldown results in less banding, which can be used for further purification of LPOR protein.

Example 2.1: Purification of LPOR Protein

All the procedures of Example 2.1 were performed in dark conditions from Step 1 to Example 4.

Step 1. Pretreatment of His-Tag Affinity Chromatography

The bacterial solution induced by the inducer was centrifuged at 5000 rpm for 20 min. Bacterial cells were collected, rinsed twice with PBS (pH=7.4), rinsed with the equilibration solution (0.1 MPBS (pH7.4), 10 mM imidazole) used for purification, and finally re-suspended with the equilibration solution (35 mL/g bacteria.) Body precipitation), ultrasonically crush the collected bacterial solution, power 200 W, ½ probe, crush for 30 s, and centrifuge again after 30 s intermittently, centrifuge at 19000 rpm for 20 min, take the supernatant, and vacuum filter with a 0.45 μm filter membrane. Then His-tag, Ni-affinity column affinity chromatography was performed.

Step 2. His-Tag Affinity Chromatography (Ni-Affinity Chromatography Column)

The protein with His is bound to Ni by affinity chromatography, and the purified protein is obtained by steps such as elution. The purification method of His-tag affinity chromatography includes equilibration, loading, washing, elution and storage. The specific operation methods are:

Equilibration: Equilibrate the prepacked column with the equilibration solution (0.1 MPBS (pH7.4), 10 mM imidazole), turn on the UV detector, adjust the wavelength to 280 nm, the sensitivity is 100%, and preheat to make the liquid flow down at a uniform speed (3 mL/min), At this time, adjust the light amount to keep the absorption value stable at 100. At this time, it is full. After the absorption value is stabilized, adjust the sensitivity to 0.5 A/0.2 A to keep the absorption value stable at 0. This is the baseline adjustment.

Sample loading: Slowly add the sample processed in advance in step 1 to the column to avoid the generation of air bubbles. Keep the flow rate as low as possible (1 mL/min). When the absorbance is greater than 20, use a 50 ml centrifuge tube to connect the outflow. Protein solution, called flow-through solution (flow-through is the bacterial protein solution that is not bound to the gel).

Washing: Slowly add binding buffer (0.1 MPBS (pH7.4), 40 mM imidazole) along the wall, turn on the switch, take more than 10 column volumes of binding buffer, the flow rate is 3 mL/min, so that the absorbance value returns to baseline or close to At baseline.

Elution: First select 50 mM imidazole as the flow wash concentration, mainly eluting bacterial protein that is not specifically bound in the gel; then use 100-500 mM imidazole as the elution concentration (100-500 mM can be eluted to obtain the target protein. The best is 300 mM), the main target protein is eluted, and the protein at each elution concentration is detected by SDS electrophoresis.

Storage: After elution, wash the column with 3 times the volume of sterilized water, inject 20% ethanol, so that the gel is fully immersed in ethanol, and store at 4° C. until use.

Step 3. Protein Concentration

Due to the low concentration of the protein purified by the affinity chromatography, column, it was concentrated using an ultrafiltration cup method before performing gel chromatography filtration. Select a 30 kd ultrafiltration cup, rinse with double distilled water three times, then add double distilled water to the ultrafiltration cup, 3000 rpm, centrifuge for 10 minutes, thoroughly clean the filter membrane, drain the double distilled water, add it to be concentrated Centrifuge the protein sample at 3000 rpm until the required volume (7 ml) is reached. Stop centrifugation. Use nanodrop to determine the protein concentration. The measured concentration is 30-50 mg/ml.

Step 4. Gel Filtration

According to the molecular weight of LPOR protein was 36.99 kd, a sephardex g-75 gel chromatography column was selected. Connect the pre-assembled column to the instrument akta-xpress. Equilibrate 1.5 column volumes with gel filtration buffer (20 mMTris pH 8.0, 150 mM NaCl, 1 mM EDTA).

Figure 6:
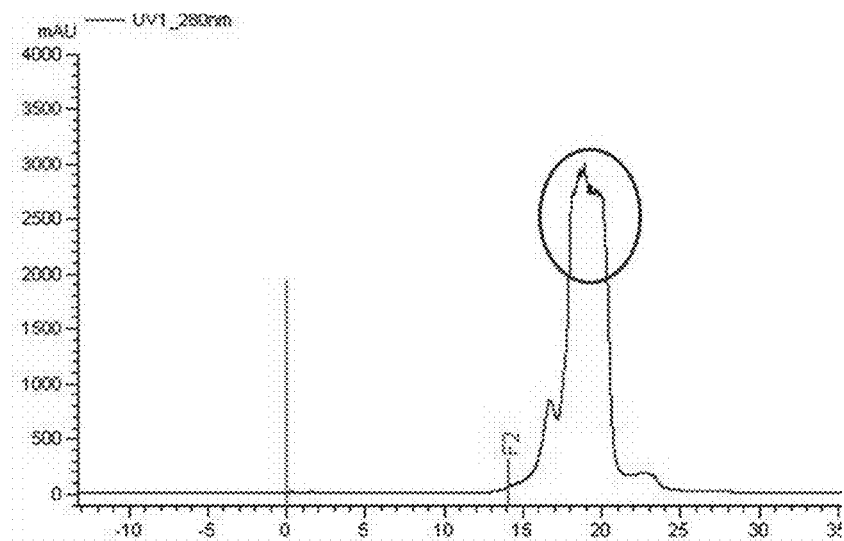
FIG. 6 is a gel filtration curve (under dark conditions) of a sample without adding NADPH enzyme.
Figure 7:
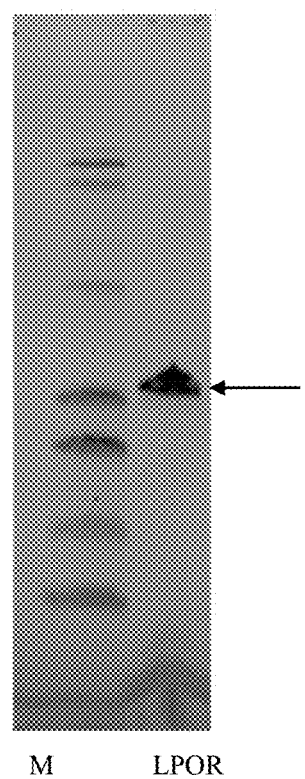
FIG. 7 is a SDS gel analysis result chart (under dark conditions) of the sample obtained from FIG. 6.

After the completion of the equilibration, inject the 7 ml sample obtained after concentration by affinity chromatography, adjust the flow rate to 1 ml/min, and turn on the UV detection system. When the protein flows out, collect the sample. Wash the column, store it for future use, and collect the sample (2 ml/tube). The gel filtration curve is shown in FIG. 6, where the circled part in the figure is the target protein, and there is only one peak, which indicates the comparison of the obtained protein Pure without breaking. Part of the collected samples were analyzed by sds-page (see FIG. 7). A protein sample with a single target band will be obtained, which is about 36 KD in size. Concentrate again with a 30 kd ultrafiltration cup (see step 3 for specific steps) to a protein concentration of 10-15 mg/ml.

Example 3: Purification of LPOR Protein (with NADP Added)

Figure 8:
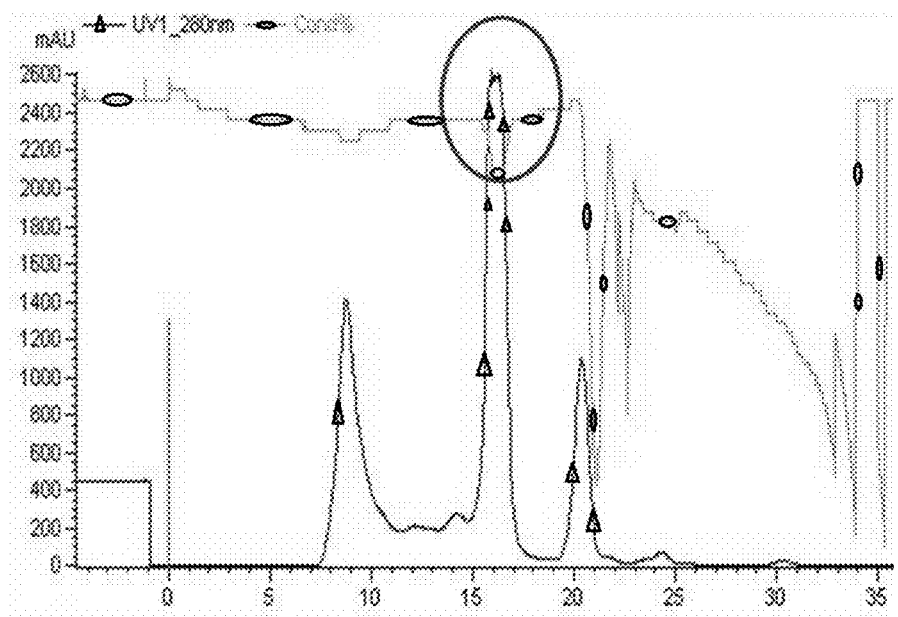
FIG. 8 is a gel filtration curve (under dark conditions) of NADPH enzyme added to the loaded sample.

In this embodiment, a part of the concentrated protein (10 ml) obtained in step (4) in example of 2.1 is added to NADPH coenzyme. The other steps are the same as those in Example 2.1, and are not repeated here one by one, and the gel filtration curve diagram is finally obtained. From FIG. 6 (without NADPH) and FIG. 8 (with NADPH added), it can be seen that NADPH coenzyme plays a certain role in stabilizing the structure of the sample. NADPH coenzyme was added before gel chromatography filtration. Positive effect on sample separation.

Example 4: Activity Analysis of LPOR Protein

Figure 9:
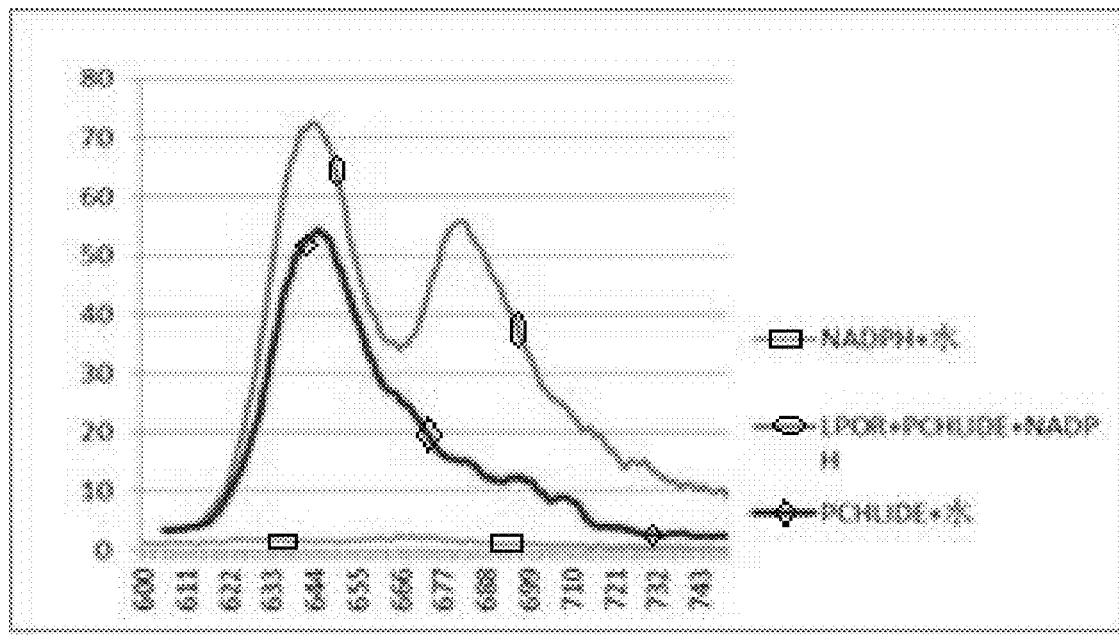
FIG. 9 is an activity analysis chart (under dark conditions) of the LPOR protein.

Take a black well-protected 96-well plate and add the following materials to A1-A4: A1 water 50 ul; A2 NADPH 0.5 ul, water 49.5 ul; A3 Pchlid (original chlorophyllate) 5 ul, water 45 ul; A4 LPOR (purified Protein) protein 5 ul, Pchlid5 ul, NADPH 0.5 ul, and water 39.5 ul. Put a 96-well plate into the nucleic acid protein detection system, set the excitation light at 450 nm, 5 s, the emission light at 600-800 nm, and detect the peak at 600-800 nm. The results are shown in FIG. 9. It is proved from FIG. 9 that the LPOR protein is an active substance, indicating that the structure of the LPOR is complete and has biological activity.

Example 2.2—Purification of LPOR Protein

Figure 10:
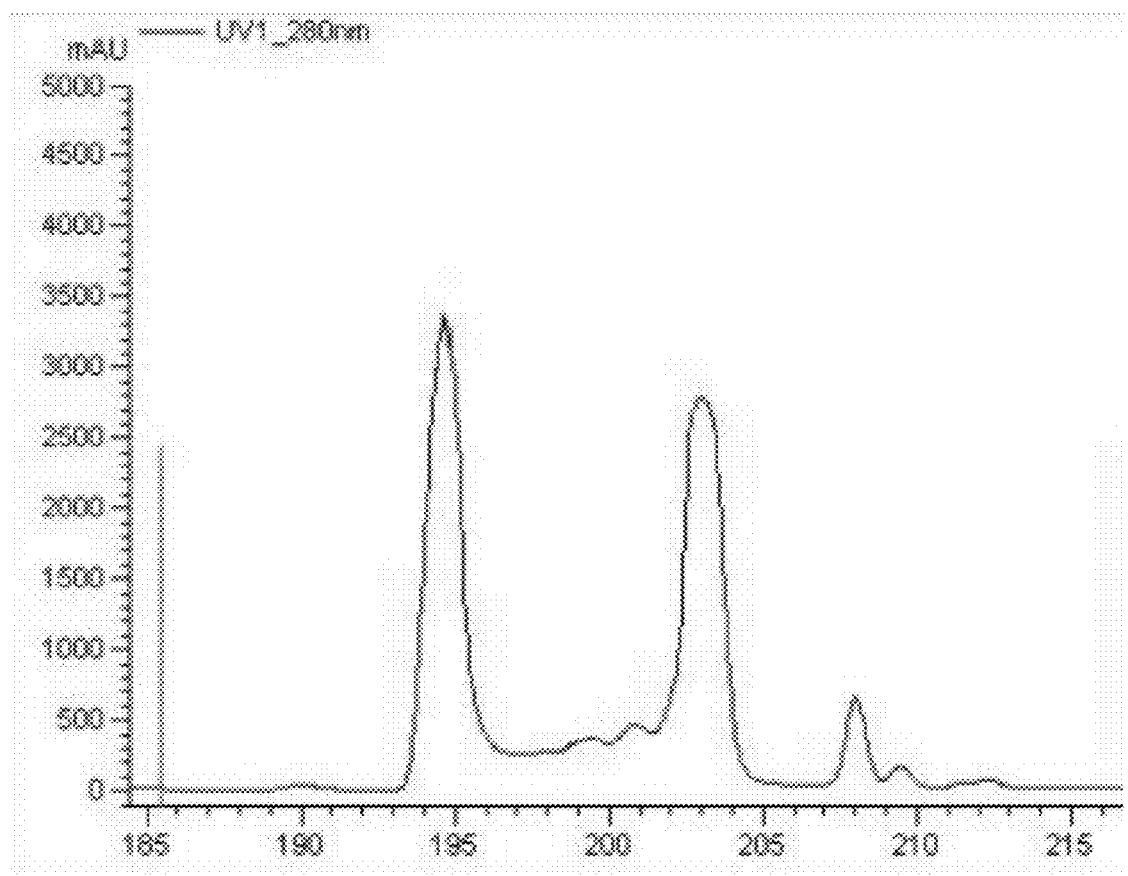
FIG. 10 is a gel filtration curve diagram of the sample without adding NADPH enzyme (under non-dark conditions and under natural light conditions)
Figure 11:
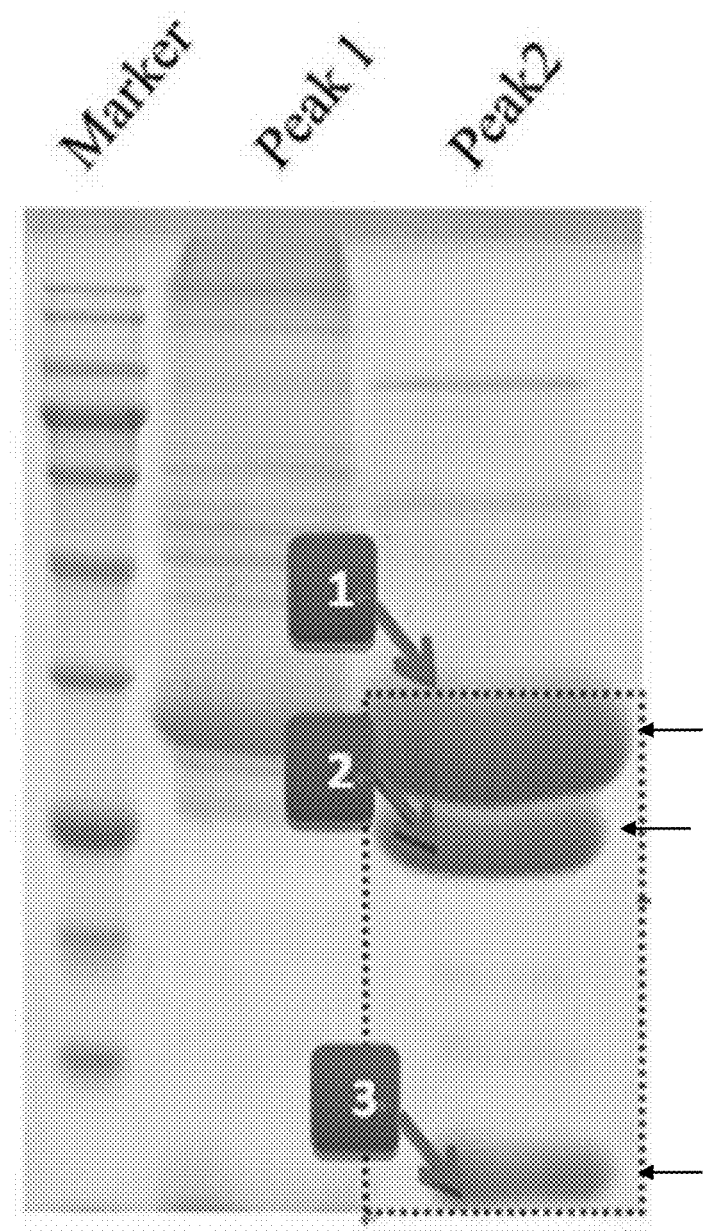
FIG. 11 shows SDS gel analysis results of the sample obtained from FIG. 10 (under non-dark conditions, under natural light conditions, the protein was broken, some were intact proteins, and some were broken proteins).

Compared with the implementation example 2.1, all conditions are the same, and the purification process is performed in a non-dark condition under a natural light environment. The results obtained are shown in FIG. 10 and FIG. 11. FIG. 10 is the filtration curve chart for the Example 2.2. FIG. 11 is an sds-page analysis chart of the collected samples. As can be seen from FIG. 11, two distinct protein peaks were obtained by gel filtration. Each collected protein peak was verified by SDS-PAGE, and the results are shown in FIG. 11, where the first lane in FIG. 11 is Marker, the second lane is the first peak in FIG. 10, and the third lane is the second peak in FIG. 10. FIG. 11 shows that the first peak obtained from molecular sieve in the second lane is other and no-target protein, and the protein obtained from the second peak of molecular sieve in the third lane is the target protein (36.66 KD). The results show three bands m the third lane, but the molecular sieve result is a clear protein peak, indicating that some of the proteins obtained in this peak have a fragmentation phenomenon(break), and the two lower molecular weight proteins (the bottom is about 10 KD and the middle is about 26 KD) are plus to exactly the molecular weight of the target protein above.

This further illustrates that for light-sensitive proteins, in order to obtain the complete protein, it is best to perform it in the dark without light, otherwise protein breakage will occur. This may be a relatively important step in the purification of photosensitive proteins, which is also an important discovery and purification step of the present invention. It is generally believed that the purification of LPOR protein does not need to be performed in the dark, and the present invention accidentally chooses to purify at night and in dark conditions to obtain the complete protein, and the fragmented non-intact protein is obtained under the condition of light, which seems to indicate that the outside environment is important for the purification conditions of the protein, and the specific mechanism is still unclear.

Example 5: Crystallization and Optimization of LPOR Protein

Step 1:

Concentrate the protein obtained in Step 2 in example 2.1 with an Amicon Ultra-30k ultrafiltration membrane, and use Nanodrop to measure the concentration and it is 30 mg/mL. Take 1 μL of the concentrated protein and verify the purity and concentration by SDS-PAGE before performing the following crystallization experiments.

Step 2: Prior Art Method for Crystallization

Figure 13:
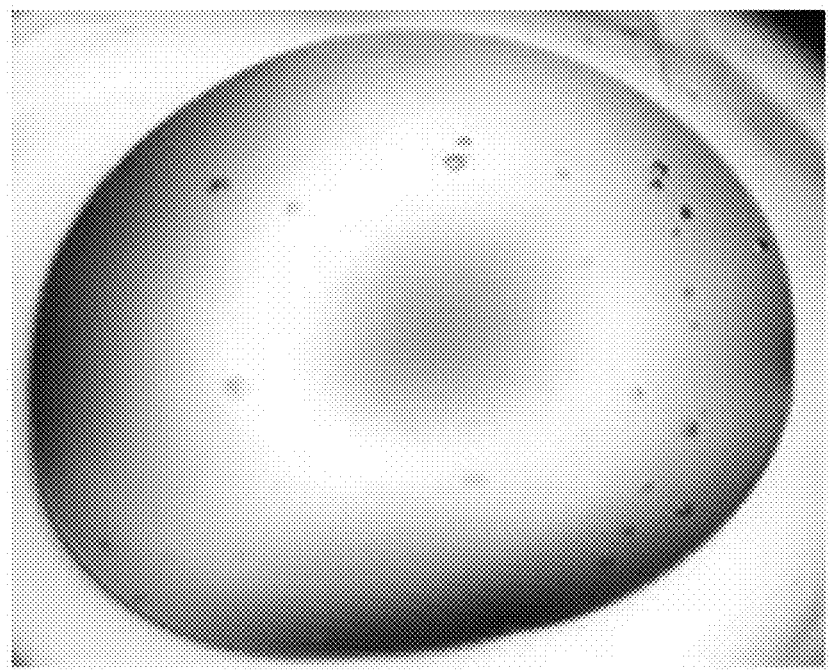
FIG. 13 shows the results of crystal experiments of LPOR protein by conventional methods.
Figure 14:
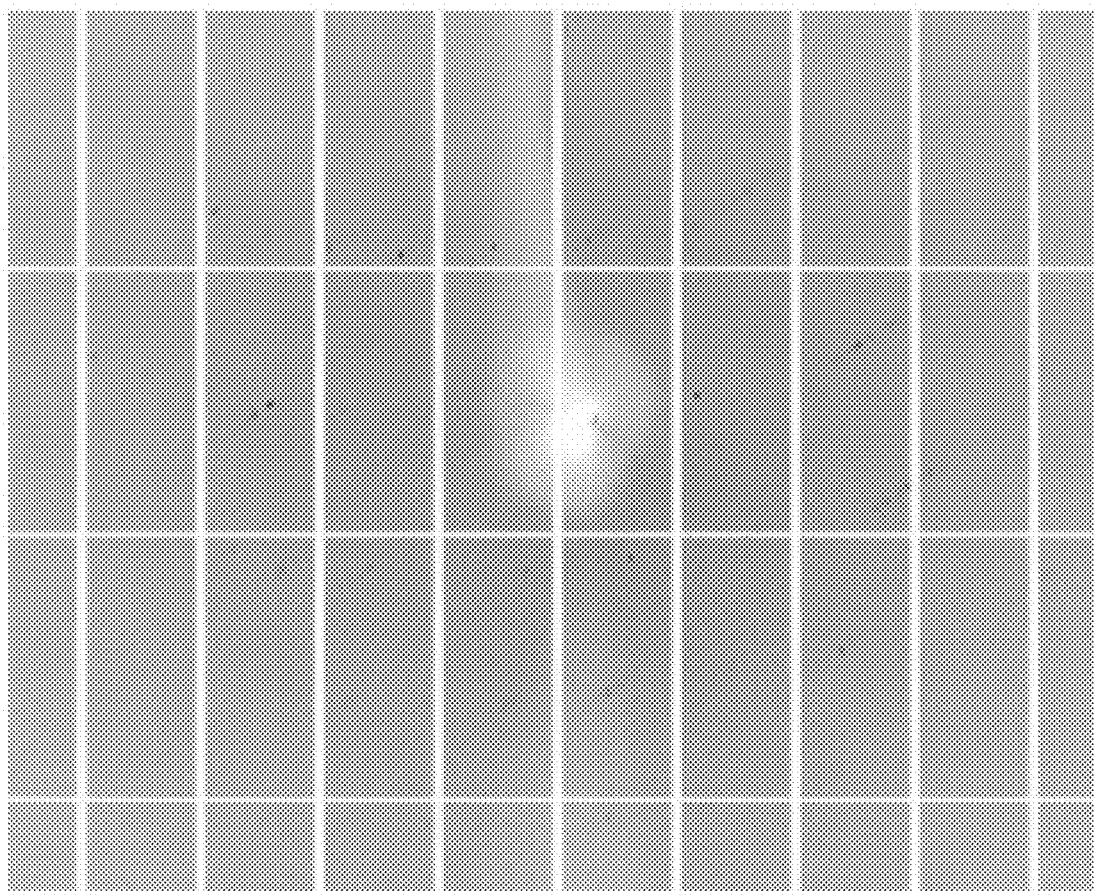
FIG. 14 shows the results of crystal experiments of LPOR protein by conventional methods.

The conventional crystallization buffer (2-methyl-2,4-pentanediol) was used to start the crystallization, and a manipulator was used to select a large number of crystallization conditions for the crystallization conditions of the long crystals. Among them, the LPOR protein crystals were subjected to X—The preliminary diffraction of ray, the crystal diffraction rate is 3.2 Å, and the results are shown in FIG. 13-14.

Figure 12:
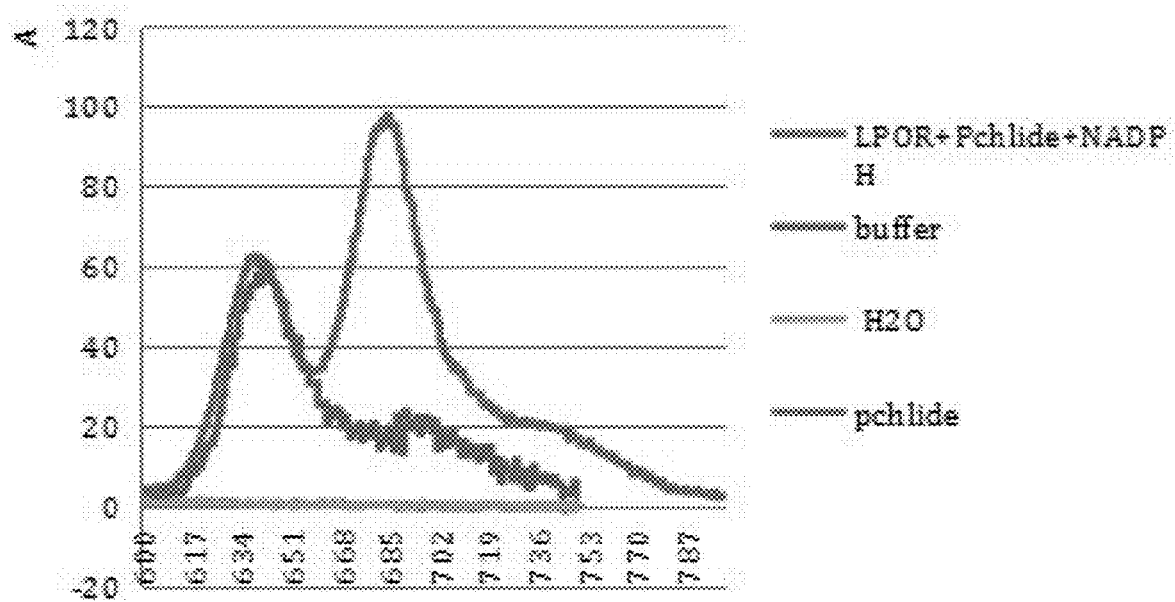
FIG. 12 is the activity measurement chart after crystallization (buffer and water are lines parallel to the X axis, Pchlide with a single peak and LPOR+Pchlide+NADPH with a double peak).

Measure the activity of the obtained LPOR protein crystals: Take a black, 96-well plate protected from light, and add the following substances to A1-A: A1 water 50 ul; A2 NADPH 0.5 ul, water 49.5 ul; A3 Pchlid 5 ul, water 45 ul; A4 protein Crystals 3-4, Pchlid 5 ul, NADPH 0.5 ul, and water 44.5 ul. Put a 96-well plate into the nucleic acid protein detection system, set the excitation light at 450 nm, 5 s, the emission light at 700 nm, and detect the peak at 700 nm. The results of the activity measurement of the obtained LPOR protein crystals are shown in FIG. 12. It can be seen from FIG. 12 that the obtained LPOR protein crystals have protease activity in the presence of Pchlide and NADPH.

Step 3: Improved Crystallization Mode 1

Figure 15:
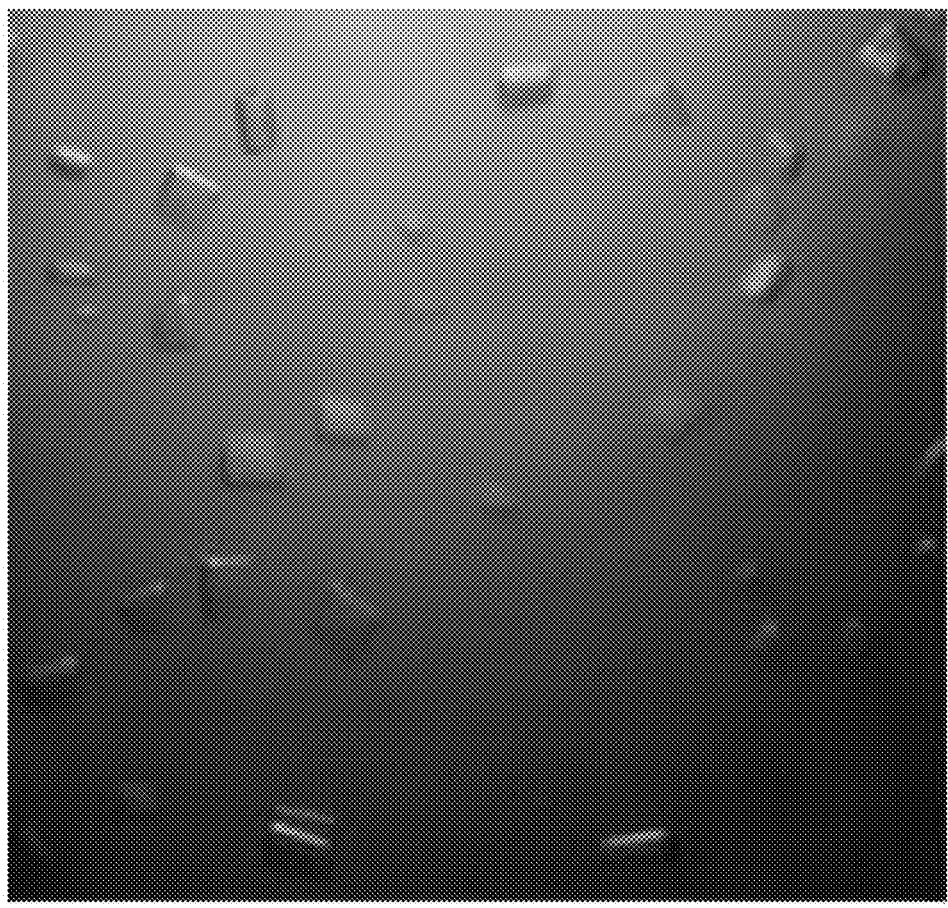
FIG. 15 is a graph showing the results of the improved LPOR protein crystallisation.
Figure 16:
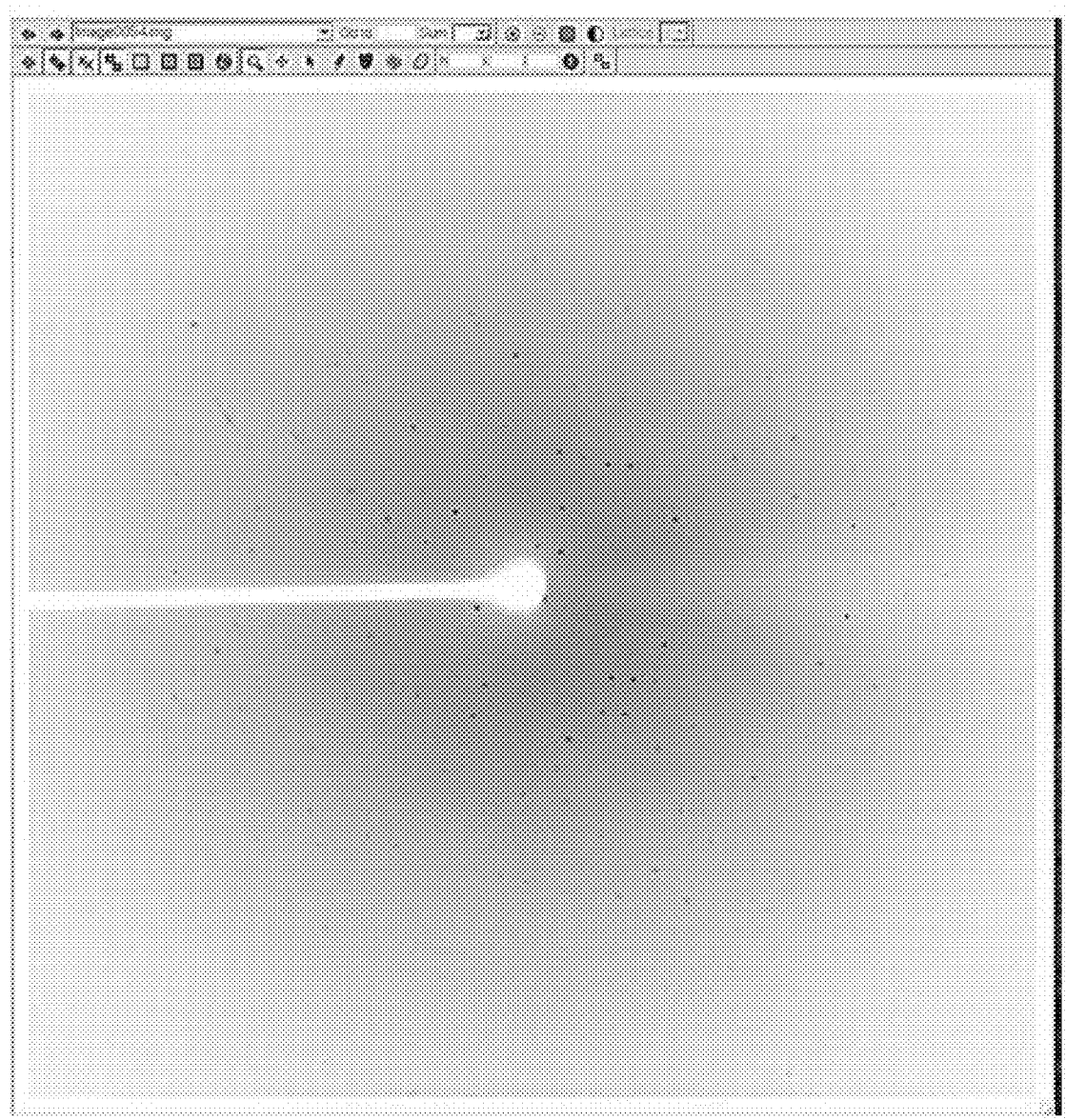
FIG. 16 is a graph of the crystallized results of the improved LPOR protein.

At the same time, the protein of step 1 was used to continue to optimize the crystallization quality of LPOR. After a large number of crystallization conditions, it was finally determined that it was a crystallization buffer composed of 18% PEG20000 and 0.1M NaAc (sodium acetate) at pH 4.5. Crystallization conditions for long crystals (using the crystal sitting drop method, growing for 10 days to reach the optimal state. Pick the crystals, and protect them in antifreeze solution (25% PEG 3350, 0.2M tri-Lithium Citrate, 10 mM NADPH, and 20% glycerol), Then put it in a liquid nitrogen tube and store it in order to collect the diffraction data], and perform a large number of point crystals to obtain better quality crystals, as shown in FIG. 15-16. After optimizing the crystal quality of LPOR, the crystals diffract. The rate can reach 2.9 Å. At the same time, the protein activity test can also be performed by referring to the method of step 2.

Step 4: Improved Crystallization Method 2

Figure 17:
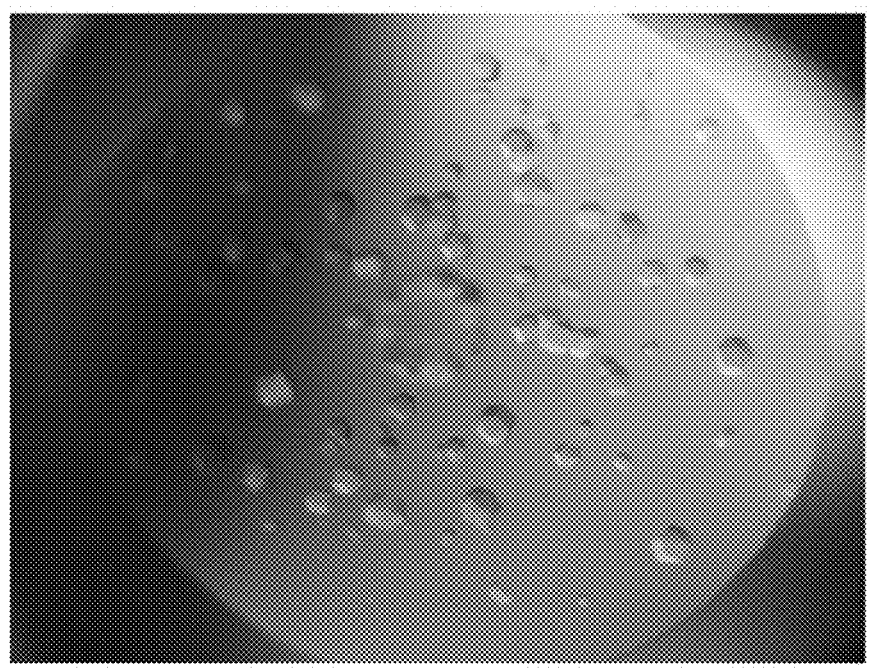
FIG. 17 is a graph showing the results of LPOR protein crystallization in an optimal manner.

At the same time, the protein of step 1 was used to continue to optimize the crystallization quality of LPOR. After a large number of crystallization conditions were selected, it was finally determined that 50 ul LMB1 A7 was added with 10 ul additive screen 10 (ZnCl2) and a robotic screen was adopted to conduct a large number of crystallization conditions for long crystals. Crystals (using the crystal sitting drop method, grow for 10 days to reach the best state. Pick the crystals and soak them in an antifreeze protection solution (25% PEG 3350, 0.2M tri-Lithium Citrate, 10 mM NADPH, and 20% glycerol). Then put it in a liquid nitrogen tube and store it for the purpose of collecting the diffraction data.] The X-ray preliminary diffraction of the obtained LPOR protein crystal was performed. The result is shown in FIG. 17. The crystal diffraction rate can reach 1.8 Å. It shows that the method of the present invention can be used. The better crystals obtained have more practical significance for studying proteins.

Example 6: LPOR-6803 Protein Acquisition and Crystallization Process

LPORs (light-dependent protochlorophyllide oxidoreductase) are soluble monomeric proteins, about 300 amino acids, which have evolved from a branch of the general family of the SDR family. The common feature of LPOR protein and SDR family is light dependence, similar to another known DNA photolytic enzyme, which contains two chromophores: FAD and MDHF/8-HDF. All LPORs proteins contain NADPH as a secondary Factor and has a Tyr-dependent catalytic site, while its substrate Pchlide itself acts as an antenna of light or another co-factor. The overall structure of LPORs crystals is very similar to an unknown SDR-like protein sequence 3rd5, both of which have 29.89% homology. The substrate binding site remains unknown. Therefore, in this embodiment, the substrate binding site and the catalytic reaction mechanism of the LPOR protein are explained by analyzing the crystal structure of the LPOR protein from another species (*Synechocystis* sp. PCC6803).

Example 6.1 Vector Construction and Protein Expression and Purification

The primer was designed according to the LPOR-6803 cDNA sequence, and the LPOR-6803 cDNA sequence (SEQ. ID NO: 4, FIG. 24, and the corresponding amino acid sequence SEQ ID NO: 13) was obtained by PCR amplification.

```
LPOR6803-N:
                                      SEQ ID NO: 5
5'-ggatccatgaaaccacggtgatcatcaccggag-3',;

BamHI site added at N-terminus;

LPOR6803-C:
                                      SEQ ID NO: 6
5'-ctcgagctaaaccagacccactaacttttcgcttag-3',;

XhoI site added at C-terminus.
```

The amplified LPOR-6803 cDNA sequence was cloned into the prokaryotic expression vector pE-SUMO3 (purchased by Saimofei) and named pE-SUMO3-LPOR6803.

The constructed prokaryotic expression vector pE-SUMO3-LPOR6803 was used to transform *E. coli* cell BL21 (DE3) and cultured at 37° C. for 3-5 hours until the OD600 reached 0.8. 0.3 mM IPTG was added and induced to culture at 28° C. for 5 hours.

The cultured cells were centrifuged at 5000 r/min, 4° C. for 30 minutes, and the supernatant was discarded. The obtained bacteria were suspended in solution A (20 mMTris-HCl, pH 7.4, 0.3 M NaCl, and 20 mM imidazole) in an ice bath.

The suspension was crushed with a high-pressure homogenizer, 8000 Pa, 3 min, and crushed 3 times; 16000 r/min, 4° C., and centrifuged for 30 min. After the supernatant was filtered through a 0.44 um filter membrane, a 5-ml HiTrap FF crude oil column was loaded. Gradient elution was performed with solution B (20 mMTris-HCl, pH 7.4, 0.3 M NaCl, and 20 Mm-300 mM imidazole) at the concentration of imidazole (20 Mm, 50 Mm, 100 Mm, 200 Mm, 300 mM).

Collect the eluted protein peaks (200 mM imidazole eluted peaks), add 4000 U/G SENP2 protease, cut off the SUMO tail, and then perform dialysis. The dialysate is solution C (20 mMTris-HCl, pH 7.4, 0.05 M NaCl). Dialysis is used to remove imidazole. Subsequently, the protein was loaded onto a 5-ml Hitrap Q HP column using a 50 mM-500 mM NaCl gradient eluent (50 mM, 100 mM, 200 mM, 300 mM, 400 Mm, 500 mM). The protein peak (300 mM NaCl) was recovered and passed through a Superdex 75 molecular sieve column.

Example 6.2 Protein Spotting and Data Analysis

Using a 30 KD millipur protein concentration tube, the obtained LPOR-6803 protein was concentrated to 26 mg/ml, and the concentration buffer was 20 mkt Tris-HCl, 150 mM NaCl.

The pool of protein spots is an equal volume of concentrated buffer and 0.2M tri-Lithium Citrate, 0.01M Zinc chloride containing 20% PEG3350. Use the crystal sitting drop method to grow for 10 days to reach the optimal state. Pick the crystals and soak them in an antifreeze protection solution (25% PEG 3350, 0.2M tri-Lithium Citrate, 10 mM NADPH, and 20% glycerol), and then put them in a liquid nitrogen tube to save the diffraction data.

The crystal was placed in SSRF BL17U to collect the diffraction data. The results are shown in Table 2 below.

TABLE 2

Statistics of crystallographic data collection and structure correction data

Figure 18:
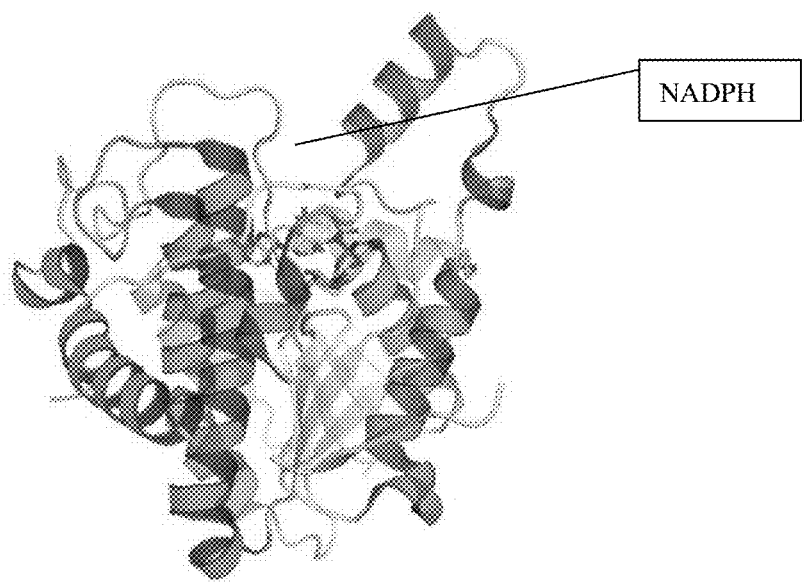
FIG. 18 is a schematic structural diagram of the binding of LPOR-6803 protein to NADPH under crystallization conditions.
Figure 19:
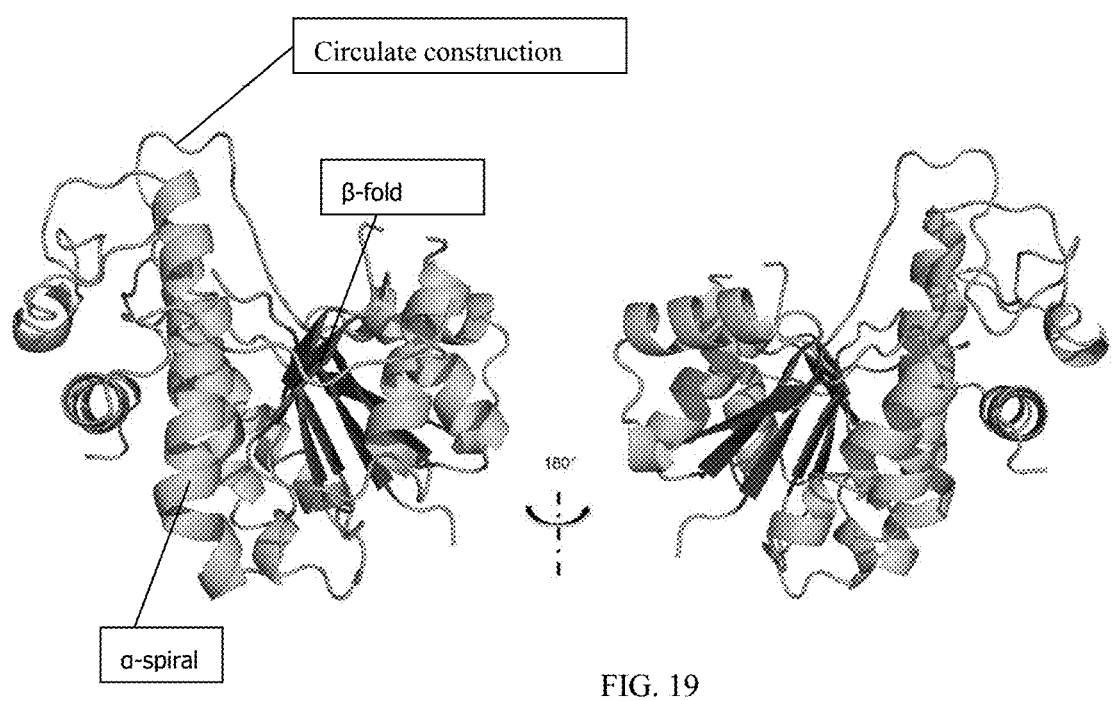
FIG. 19 is a three-dimensional spatial structure diagram of the LPOR protein. The construction of the single protein of the thermosy nechococcus elongates LPOR. The right is rotating 180 degrees of the left.
Figure 20:
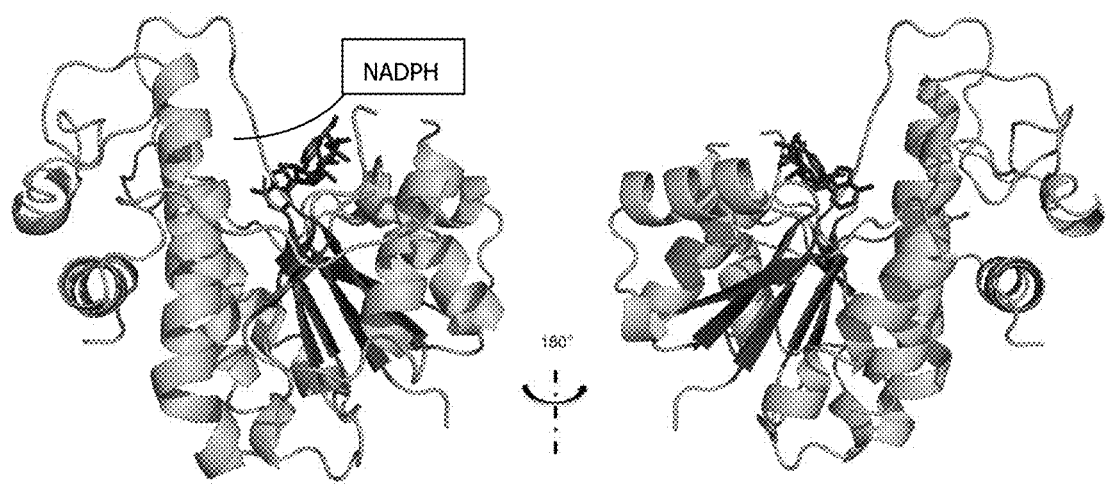
FIG. 20 is a schematic diagram of the spatial structure of the LPOR protein binding to NADPH. The construction of the single protein of the thermosy nechococcus elongates POR-NADPH.
Figure 21:
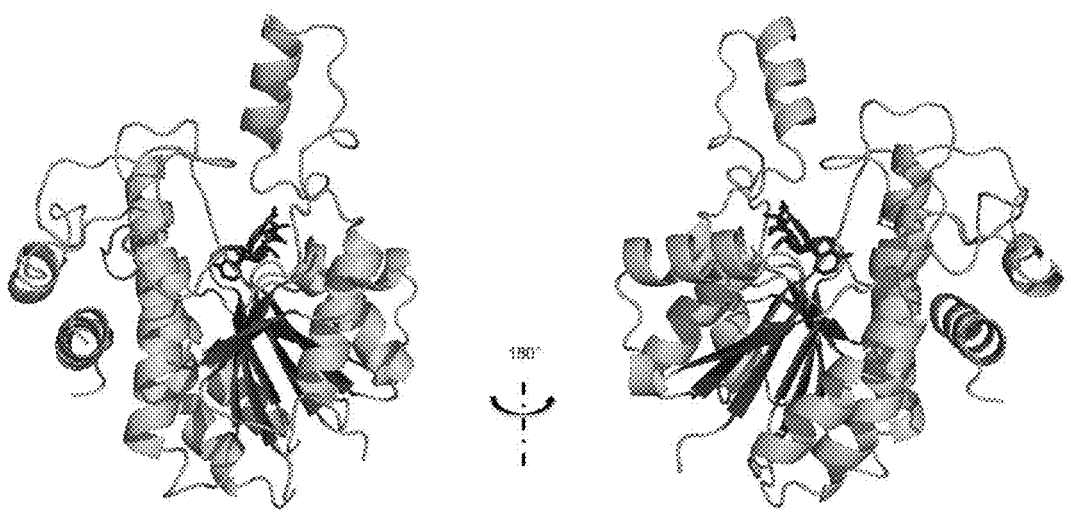
FIG. 21 is the protein structure of synechocystis POR-NADPH complex.

| Parameter | 6803/nadph (6G08) |
|---|---|
| data collection | |
| Space group | P21 2 21 |
| a, b, c (Å) | 56.96, 72.89, 155.99 |
| a·, β, γ (°) | 90.00, 90.00, 90.00 |
| Wavelength (Å) | 0.97851 |
| Resolution (Å) | 77.99-1.87; 28.57-1.87 |
| Signal to noise ratio | 2.24 (at 1.87 Å) |
| Completion (%) | 94.9; 95.0 |
| Data Error/Structure Correction | 0.10 |
| R factor, free R factor | 0.170, 0.199 |
| | 0.179, 0.207 |
| Wilson B-factor | 20.3 |
| Anisotropy | 0.479 |
| Solvent factors Ksol, Bsol | 0.41, 51.3 |
| Twin L-test | <│L│> = 0.49 |
| | <L²> = 0.32 |
| Fo, Fc correlation coefficient | 0.96 |
| Total number of atoms | 5282 |
| Overall atomic mean B factor | 25.00 |
| Lagrangian distribution (optimal zone/ non-allowable zone %) | 97.68/0 | a) Intensity data estimated from amplitude data
b) The theoretical values of b │L│ and │L2│ are set to 0.5 and 0.333 for the non-center symmetric diffraction points of the non-twin data, and 0.375 and 0.2 for the perfect twin data. It was found that the diffraction data of the LPOR6803 protein crystal was 1.8 Å, and the structure of the protein could be clearly seen. When it was combined with NADPH, the NADPH binding site was also clearly visible, as shown in FIG. 18. This further illustrates that having a metal salt solution in a crystallization buffer solution has a very good crystallization effect on LPOR.

Example 7: Preparation Method of LPOR-Y193F Mutant Protein Crystal

LPORs are soluble monomeric proteins, about 300 amino acids, which have evolved from a branch of the general family of the SDR family. The LPOR protein and the SDR family are characterized by light dependence. Similar to another known photoenzyme DNA photolyase, it contains two chromophores: FAD and MDHF/8-HDF. All LPORs proteins contain NADPH as a cofactor and have a Tyr-dependent catalytic site. At the same time, its substrate Pchlide itself acts as an antenna of light or another common factor. The overall crystal structure of LPORs is very similar to an unknown SDR-like protein sequence, with 29.89% homology. 3rd5 comes from *Mycobacterium partuberculosis*, which also makes LPORs crystals the best modeling template to date. However, to obtain the x-ray crystal structure of the LPOR protein and solve the phase problem, heavy metal derivatives are still needed.

Therefore, the analysis of the crystal structure of the LPOR-Y193F mutant protein to lay the foundation for the structural analysis and phase determination of the LPOR protein is a problem that needs to be urgently solved by those skilled in the art.

Example 7.1 LPOR-Y193F Mutant Protein Expression

The LPOR cDNA Y193F mutation primer was designed, and the mutated LPOR-Y193F cDNA sequence was obtained by using the KOD Plus mutagenesis kit (TYOBO) as SEQ ID NO 7; the LPOR cDNA Y193F mutation primer was SEQ ID NO 8 and SEQ ID NO 9, and the obtained LPOR-Y193F cDNA was cloned into the prokaryotic expression vector pE-SUMO3, and the prokaryotic expression vector pE-SUMO3 was purchased from Youbao Biological to obtain pE-SUMO3-LPOR-Y193F. For example, FIGS. 26-28 show the mutated and non-mutated nucleic acid and amino acid sequences.

Transfer pE-SUMO3-LPOR-Y193F into *E. coli* BL21 cells and incubate at 37° C. for 5 hours until the OD600 reaches 0.8. Add an inducer at 28° C. and culture for 5 hours to obtain a bacterial suspension; 0.3 mM isopropyl-β-D-thiogalactoside. *E. coli* BL21 was purchased from Tiangen Biological Company.

The obtained bacterial suspension was 5,000 rpm, 4° C., centrifuged for 30 minutes, and the supernatant was discarded. The obtained bacterial suspension was suspended in solution A in an ice bath to obtain a suspension, where the solution A was 20 mM. Tris-HCl, 0.3M NaCl and 20 mM imidazole. Its pH is 7.4. The suspension was crushed with a high-pressure homogenizer. The homogeneous crushing conditions were 8000 pressure, 3 minutes, 3 times of crushing, and then centrifuged for 30 minutes. The centrifugation conditions were 16,000 rpm, 4° C. to obtain the suspension supernatant.

Example 7.2—Purification of LPOR-Y193F Mutant Protein

The obtained suspension supernatant was filtered through a 0.44 um filter, and a 5-ml HiTrap FF crude oil column was loaded and eluted with an imidazole concentration gradient using solution B, where solution B was composed of 20 mM Tris-HCl, 0.3M It consists of NaCl and 0.02-0.3M imidazole and has a pH of 7.4. The eluted protein peaks were collected, the SENP2 protease was added, the SUMO tail was cut off, and then dialyzed against solution C, which was composed of 20 mMTris-HCl and 0.05 M NaCl and had a pH of 7.4. Subsequently, the protein was loaded on a 5-ml Hitrap Q HP column with a gradient of 0.05-0.5M NaCl as eluent; the protein peak was recovered and passed through a Superdex 75 molecular sieve column to obtain the LPOR-Y193F mutant protein.

Example 7.3—Crystallization of LPOR-Y193F Mutant Protein

The millipur protein concentration tube 30 KD was used to concentrate the obtained LPOR-Y193F mutant protein to 26 mg/ml, where the concentration buffer included 20 mM Tris-HCl and 150 mM NaCl. The crystals were grown in the pool of protein spot crystals for one week to reach the optimal state. The protein spot crystal pool solution includes equal volume of concentrated buffer and solution D; solution D is composed of 0.1M sodium dimethylformate buffer, 0.01M zinc chloride and 1.4M sodium acetate, and its pH is 6.5. Pick the crystals and soak them in the antifreeze protection solution for 5 s, and then store them in a liquid nitrogen tube to collect the diffraction data. The antifreeze protection solution is 1.4M sodium acetate, 0.1M sodium dimethylformate buffer, 0.01M. It consists of zinc chloride, 10 mM NADPH and 20% glycerol, and its pH is 6.5. The obtained LPOR-Y193F mutant protein crystal was put into SSRF BL17U to collect diffraction data. The results are shown in Table 3. Among them, according to Table 3, the diffraction data of the LPOR-Y193F mutant protein crystal is 2.50 Å. The invention discloses a method for preparing a LPOR-Y193F mutant protein crystal, thereby the structure of the LPOR-Y193F mutant protein crystal is analyzed to lay the foundation for the structural analysis and phase determination of the LPOR protein. At the same time, it lays the foundation for thoroughly elucidating and determining the catalytic mechanism of light-sensitive superspeed proteins or engineering it.

TABLE 3

Diffraction data of LPOR-Y193F mutant protein crystals
Crystallographic data collection and refinement statistics

| Parameter | IporY193 F/nadp (6G06) |
|---|---|
| Data collection | |
| Space group | P 63 2 2 |
| Cell dimensions | |
| a, b, c (Å) | 134.95, 134.95, 104.75 |
| α, β, γ(°) | 90.00, 90.00, 120.00 |
| Wavelength (Å) | 0.97776 |
| Resolution (Å) | 116.87-2.50; 78.00-2.50 |
| $<I/\sigma(I)>1^a$ | 2.09(at 2.51 Å) |
| Completeness (%) | 99.8; 99.8 |
| Rmerge | 0.08 |
| Refinement | |
| R. Rfree | 0.196, 0.249 |
| | 0.202, 0.253 |
| Wilson B-factor (Å2) | 55.8 |
| Anisotropy | 0.543 |
| Bulk solvent ksol(e/Å$^2$), Bsol(Å$^2$) | 0.35, 48.3 |
| L-test for twinning$^b$ | $<\|L\|> = 0.47$ |
| | $<L^2> = 0.30$ |
| Fo, Fc correlation | 0.95 |
| Total number of atoms | 2217 |
| Average B, all atoms (Å$^2$) | 70.0 |
| Ramachandran plot(favored/outliers, %) | 96.63/0 |

$^a$Intensities estimated from amplitudes.
$^b$Theoretical values of $<\|L\|>$, $<L2>$ for acentric re_actions are 0.5, 0.333 respectively for untwinned dataset, and 0.375, 0.2 for perfectly twinned datasets.

Example 8 Binding Site and Spatial Structure of LPOR Protein and Application

The invention discloses the structural basis of the catalytic action of POR protein in the chlorophyll biosynthetic pathway, which is a very important one-way energy flow in the biosphere that converts light energy into chemical energy. As a light-driven response in chlorophyll biosynthesis, the catalytic effect of POR is the trigger for seed germination, which causes profound changes in plant morphological development. In view of this important biological role, POR has become the focus of many biophysical studies. The combination of the most advanced time-resolved and cryo-electron microscopy techniques, for cyanobacteria and higher plants, the detailed mechanism of action of POR enzymes in different photosynthetic tissues was analyzed in detail. The kinetics of the picosecond excited state of the original chlorophyllate stimulated the interaction between the substrate and the active site disability, which is a necessary process to trigger subsequent chemical reactions. This includes the sequential transfer of hydrides from NADPH and the transfer of protons from active site residues or solvents.

Proton transfer relies on solvent dynamics and an implicit network of elongin movement that occurs on the microsecond scale. The hydride transfer of NADPH is not synergistic, but occurs gradually, including the electron transfer from the excited state of the original chlorophyllate of NADPH, and the subsequent proton-coupled electron transfer. This is the first case of biologically reported gradual transfer of hydrides. These time-resolved studies have provided unprecedented insights into catalytic chemistry on a wide range of time scales (fs-s), but the structural basis required for POR photocatalysis remains elusive. The purpose of this study is to understand how excited state chemistry, bonding/breaking, and photocatalytic kinetics, substrate binding, and product release are controlled by protein structure.

In the present invention, the crystal structure of POR enzyme monomer (from *Thermosynechococcus, Elongatus*) and NADPH-POR protein complex (from *Synechocystis* and T. elongatus, respectively) are first described. 19-21). As members of the short-chain dehydrogenase/reductase (SDR) family, different forms of POR proteins are similar in structure to other members of the SDR family. 6 alpha helices around the periphery. In the structure of the POR protein from T. elongatus, closed loops between 146-160, 228-255, and 284-291 were not observed, indicating that these are mobile regions of the protein, which are related to the POR monomer and NADPH—The structural dynamics of POR-binding proteins are consistent.

However, they are present in the Synechocystis POR-nadph binding structure and play a role in coenzyme/substrate binding in two of these regions. Extending from the β-sheet, a cyclic structure consisting of residues 223-229 of the nicotinamide portion of NADPH is responsible for coenzyme binding. Similar loops have also been observed at the cofactor binding sites of other SDR enzymes, and it has been shown that coenzyme binding expands the surrounding ring structure to form two short alpha helices that, like lids, cover the active site and form a "closed" conformation.

Although, in the Synechocystis POR structure, only one long α-helix (230-239 residues, referred to as "helix 1"), and an additional circular structure (148-159 residues, "loop 1") were observed. The central β-sheet extends out and also appears near "Helix 1." The data show that "Loop 1" is very conserved in the POR protein, and "Helix 1" regulates subsequent prochlorophyllate substrate binding.

Outside the circular region, different POR crystal structures identify other residues that are important for coenzyme binding. SDR family proteins use Asn-Ser-Tyr-Lys to catalyze the tetrad for proton transfer and stabilize the reaction intermediate, but in the POR protein, a highly conserved Thr residue replaces the Ser residue. The crystal structure of the binary POR-NADPH complex (numbered T. longatus POR) indicates that the three residues Asn90, Tyr193 and Lys197 are directly bonded to NADPH hydrogen bonds. In addition, Arg38, Lys42, and Asp63 interact with NADPH through a hydrogen bond network of 2'phosphate molecules. Arg38 is related to coenzyme binding/release. In different POR structures, Arg38 has similar positions but has different conformations. In the POR monomer structure, Arg38 only forms a link with the solvent and does not interact with any other residues. However, in the Synechocystis and T elongates POR-NADPH structure, Arg38 not only interacts with the 2-phosphate group of NADPH, but the guanidyl group of Arg38 also stacks with the adenine of NADPH. It completely surrounds the end of the coenzyme and forms a closed Coenzyme binding bag. Arg has a different conformation, indicating that it is a very important base for coenzyme binding and release, and the reduced NADPH affinity of the R38V variant also illustrates this. A water channel surrounding the active sites Tyr193 and Lys197 bases was also found in these structures, which may be a potential proton relay network in the catalytic process.

Using site-directed mutants and Pchlide substrate analogs to substitute for activity, binding, and inhibition experiments to study the effects of the structure and model of ternary complexes on photocatalysts has potential significance for studying the mechanism of POR enzymes). Pchlide analogs have changed the nature of the substituents on ring E, the central Mg ion and the C17 carboxylic acid side chain have been changed, all of which are considered to play an important role in por-catalyzed photoreduction. A substrate analog, the C17 propionic acid side chain is exchanged for a methyl ester group and does not bind to POR. Moreover, this analog is not a competitive inhibitor of natural enzyme-catalyzed reactions. This is consistent with our structural model, confirming once again the importance of the propionic acid side chain in binding Pchlide to the POR active site. Mutants of Lys197 or Thr145 also cause impaired POR's ability to bind to Pchlide substrates. This conclusion is consistent with the formation of a salt bridge/hydrogen bond when these amino acid residues interact with the propionic acid side chain of Pchilde.

Other Pchlide analogs modified at different positions of the porphyrin ring have the ability to bind to POR enzymes. Although these analogs have reduced affinity compared to Pchlide itself, they can also act as competitive inhibitors. The loss of the central $Mg^{2+}$ ion and the keto group (C13 position) caused an increase of Kd of about 3-5 times, which is consistent with our hypothesis. During the substrate binding process, it is necessary to bind through coordination with water molecules in the active site. In the original structure, Lys156 was located in the lid ring region and it could directly interact with Pchlide. However, the results of the activity measurement of the K156A mutant showed that Lys156 is not important for binding, and that in the final model of the ternary complex, the hydrogen bond between lys156 and Pchlide is lacking. These two results confirm each other, indicating that Lys156 is not important.

Although Tyr223 and Pchlide have no direct effect in the ternary complex model, it promotes the binding of Pchlide in the direction required for catalysis. MD simulation results also show that in the middle stage of the substrate binding process, Tyr223 and keto groups Themesophase forms hydrogen bonds. The experimental data showed that Pchlide had significantly reduced PORs protein binding to Y223A and Y223F variants, and the MD simulation was consistent with the experimental data in this regard (FIG. 12).

The POR crystal structure and the POR-Pchlide-NADPH ternary complex structure model described in the present work provide the basic principles of photo-induced catalysis of POR proteins that are urgently needed in photosynthesis research. An extensive hydrogen-bonding network was found between the active site amino acid and Pchlide, which may be essential in photochemistry, or it may be to strengthen the excited state, creating an electron deletion site at the C17-C18 double bond. The $Mg^{2+}$ ion at the center of the Pchlide substrate and the keto group at the C13 position are also very important for photochemistry (presumably due to the role they play in the charge separation between Pchlide molecules when excited.

According to the ternary complex model proposed in this paper, the active site structure of POR is finely adjusted to promote the separation of excited state charges and stabilize the bipolar molecules that are subsequently formed on Pchlide molecules. The positive end of the bipolar molecule is located in the hydrophobic capsule of the active site and may be stabilized by π-π stacking with the conserved Phe residue. In contrast, the negative end of the bipolar molecule is located in the opposite region. In particular, the interaction between the propionic acid side chain at the C17 position of Pchlide and Thr145 and Lys197 is essential for excited state chemistry, as any change in one residue will cause photochemical damage. These excited state interactions need to facilitate the transfer of hydrides from NADPH cofactors by creating a highly polarized C17-C18 double bond. Tyr193, which is close to the active site, plays a role in stabilizing the highly active, polarized double bond. Previous studies have shown that Tyr193 is essential for efficient photochemical reactions. However, Tyr223 does not seem to be important for this process, as Y223A and Y223F mutants can still efficiently transfer hydrides from NADPH, which is consistent with the lack of a direct interaction between Tyr223 and Pchlide in our model.

The donor-acceptor distance between the pro-S hydrogen of the NADPH nicotinamide ring and the C17 position of the Pchlide molecule is 4.5±0.3 Å, however, this distance may be slightly reduced during photoexcitation to promote the effectiveness of photoactivated hydrides Transfer. Protons from the highly conserved Tyr193 residue will then be transferred to the C18 position of Pchlide. In our model, the Tyr193 residue is located at a donor-acceptor distance of 4.9±0.4 Å. In reactions catalyzed by other members of the SDR family, the catalytic Tyr is supplemented by a proton transfer mechanism. Based on the crystal structure, neighboring Lys197 is a strong candidate for proton supplementation. However, since the mutants of Y223A and Y223F show a significant reduction in the rate of proton transfer, the water network coordinated by Tyr223 may also play an important role in the proton transfer mechanism.

The elucidation of POR crystal structure and the subsequent modeling of ternary complexes constitute a major breakthrough in our understanding of how protein structure controls the catalysis of this important light-driven enzyme. We have proven that the protein structure of the active site is highly tuned to promote photochemistry, and therefore, it provides important insights on how to use light energy to drive enzyme catalysis. This work paves the way for detailed computational analysis that provides quantitative energy-understood reactions, and the description of the catalytic effect will be more complete, which is also a major challenge in enzymology at present. This work provides the key missing link between the structure of POR protein and excited state chemistry, and is of great significance for the design of photocatalytic chemical and biological catalysts.

The embodiments in this specification are described in a progressive manner. Each embodiment focuses on the differences from other embodiments. For the same and similar parts between the embodiments, refer to each other. For the device disclosed in the embodiment, since it corresponds to the method disclosed in the embodiment, the description is relatively simple, and the relevant part may refer to the description of the method.

The above description of the disclosed embodiments enables those skilled in the art to implement or use the present invention. Various modifications to these embodiments will be apparent to those skilled in the art, and the general principles defined herein may be implemented in other embodiments without departing from the spirit or scope of the invention. Therefore, the present invention will not be limited to the embodiments shown herein, but should conform to the widest scope consistent with the principles and novel features disclosed herein.

The invention claimed is:

1. A method for protein crystallization of a light-dependent protochlorophyllide oxidoreductase (LPOR), the method comprising: providing a purified and concentrated LPOR protein sample, and crystallizing the sample in a crystallization buffer at pH 4.5 to obtain a crystal protein, wherein the crystallization buffer comprises 18% PEG20000 and 0.1M sodium acetate.

2. The method according to claim 1, wherein the LPOR protein is concentrated through an AMICON Ultra-30k ultrafiltration membrane, and the concentration is 30 mg mL as measured by NANODROP.

3. The method according to claim 1, the method further comprises the following purification steps:
step 1: His-tag affinity chromatography;
step 2: protein concentration;
step 3: gel filtration,
wherein steps 1-3 are performed under dark conditions.

4. The method according to claim 3, wherein a crude protein extract having protein LPOR is pre-treated before step 1, said pretreatment comprising the following steps:
centrifuging a bacterial solution induced by an inducer;
collecting bacterial cells and washing the bacterial cells with a cleaning solution, and
then rinsing the bacterial cells with an equilibrium solution, and
finally re-suspending the bacterial cells with 35 mL/g of the equilibrium solution to form a collected bacterial solution;
wherein the collected bacterial solution is broken ultrasonically, a supernatant is taken after centrifuging the broken bacterial solution, and the supernatant is filtered through a vacuum.

5. The method according to claim 3, wherein the step of His-tag affinity chromatography comprises: equilibrating, sample loading, binding, washing and eluting, and preserving the LPOR protein solution.

6. The method according to claim 5, wherein the equilibration step comprises:
equilibrating a pre-packed column with a balance solution;
turning on a ultraviolet detector, adjusting a wavelength to 280 nm, a sensitivity being 100%, and making the liquid flow down at a constant speed of 3 mL/min; adjusting the light amount to keep an absorption value stable at 100; after the absorption value is stabilized, adjusting the sensitivity to 0.5 A/0.2 A to keep the absorption value stable.

7. The method according to claim 5, wherein the sample loading step comprises:
slowly adding the sample into the column to avoid generation of air bubbles, keeping the flow rate of about 1 mL/min; and
when the absorption value is greater than 20, using a 50 ml centrifuge tube to connect the effluent protein solution to collect the flow-through, wherein the protein in the flow-through is bacterial protein that is not bound to the gel.

8. The method according to claim 5, wherein the binding step comprises:
slowly adding binding buffer with a volume greater than 10 column volumes, and a flow rate of 3 mL/min to return the absorption value to a baseline or close to a baseline.

9. The method according to claim 5, wherein the washing and elution steps comprise:
washing the column with 50 mM imidazole to elute bacterial proteins that are not specifically bound in the gel; and
eluting by adding 100-500 mM imidazole elution buffer to elute the target protein;
wherein the protein concentration is detected by SDS electrophoresis.

10. The method according to claim 1, wherein the protein is obtained by in vitro expression.

11. The method according to claim 2, wherein the protein is obtained by in vitro expression.

12. The method according to claim 10, wherein the nucleic acid sequence of the expressed protein is a full-length sequence as set forth in SEQ ID NO: 3.

13. The method according to claim 12, wherein the nucleic acid sequence is expressed in one of prokaryotic expression vectors: pEHISTEV, pBADHISTEV1, pEBMSCHIS, or pEBSRCTEVC10HIS.

14. The method according to claim 13, wherein the prokaryotic expression vector is pEBSRCTEVC10HIS.

15. The method according to claim 14, wherein the expression vector is transformed into *Escherichia coli* C43.

16. The method according to claim 4, wherein the induction conditions are 7° C. and 0.4 mM IPTG.

\* \* \* \* \*

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
tcatgaatga gtgatcagcc acg                                          23

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
ggatccggcc aatcccacca gttttc                                       27

<210> SEQ ID NO 3
<211> LENGTH: 975
<212> TYPE: DNA
<213> ORGANISM: Artificial Sequence
<220> FEATURE:
<223> OTHER INFORMATION: Synthetic

<400> SEQUENCE: 3 atgaacaac cgatgaaacc cacggtgatc atcaccggag cctcctccgg ggtgggatta    60
tacggagcta aagctttaat tgacaaaggt tggcacgtga ttatggcctg ccgcaatttg   120
gataaaaccc agaaagtagc cgatgaattg ggttttccca aggattccta caccatcatc   180
aaattggatt tgggctatct ggacagtgtg cgccgctttg tcgcccagtt tcgggaattg   240
ggtcgtcccc tcaaagctct ggtttgtaat gcggcggttt attttccttt gctggacgaa   300
```

```
cccctctggt cagcggatga ctatgaactt tctgtggcga ccaaccacct ggggcacttt      360
ttgctttgca atctgttgtt ggaagattta aaagcctgtc ccgatgcaga taagcgttta      420
atcattttgg gcactgttac ggccaacagc aaagaactag ggggtaaaat tcccatcccc      480
gccccgccgg atttgggcaa ctttgaaggg tttgaagcgg gctttaagaa acccattgcc      540
atgattaata acaaaaaatt caaatcgggc aaagcgtata agatagtaa gctctgcaat       600 atgctcacca ccagggagtt gcaccgtcgc ttccaccaag aaacgggcat cgttttaat       660 tctctctatc cgggctgtgt agccgatact cccctattcc gcaatcacta ttccttgttc      720
cgcaccattt ttccctggtt ccagaaaaac gttaccaaag gctatgtcag ccaagaattg      780 gcagggaac gggtggccat ggtggtggcc gatgacaaat ttaaggattc tggggtgcat       840
tggagctggg gcaaccgtca acaagcgggc cgggaagcct ttgtgcagga actttcggaa      900
cagggaagcg atgcccaaaa agctcagcgc atgtgggatc taagcgaaaa gttagtgggt      960
ctggtttagc tcgag                                                      975

<210> SEQ ID NO 4
<211> LENGTH: 969
<212> TYPE: DNA
<213> ORGANISM: Artificial Sequence
<220> FEATURE:
<223> OTHER INFORMATION: Synthetic

<400> SEQUENCE: 4
atggaacaac cgatgaaacc cacggtgatc atcaccggag cctcctccgg ggtgggatta      60 tacgagcta aagctttaat tgacaaaggt tggcacgtga ttatggcctg ccgcaatttg       120
gataaaaccc agaaagtagc cgatgaattg ggttttccca aggattccta caccatcatc     180
aaattggatt tgggctatct ggacagtgtg cgccgctttg tcgcccagtt tcggaattg      240 ggtcgtcccc tcaaagctct ggtttgtaat gcggcggttt attttccttt gctggacgaa    300
cccctctggt cagcggatga ctatgaactt tctgtggcga ccaaccacct ggggcacttt     360
ttgctttgca atctgttgtt ggaagattta aaagcctgtc ccgatgcaga taagcgttta     420
atcattttgg gcactgttac ggccaacagc aaagaactag ggggtaaaat tcccatcccc    480
gccccgccgg atttgggcaa ctttgaaggg tttgaagcgg gctttaagaa acccattgcc    540
atgattaata acaaaaaatt caaatcgggc aaagcgtata agatagtaa gctctgcaat     600 atgctcacca ccagggagtt gcaccgtcgc ttccaccaag aaacgggcat cgttttaat    660 tctctctatc cgggctgtgt agccgatact cccctattcc gcaatcacta ttccttgttc   720
cgcaccattt ttccctggtt ccagaaaaac gttaccaaag gctatgtcag ccaagaattg   780 gcagggaac gggtggccat ggtggtggcc gatgacaaat ttaaggattc tggggtgcat    840
tggagctggg gcaaccgtca acaagcgggc cgggaagcct ttgtgcagga actttcggaa   900
cagggaagcg atgcccaaaa agctcagcgc atgtgggatc taagcgaaaa gttagtgggt   960
ctggtttag                                                            969

<210> SEQ ID NO 5
<211> LENGTH: 34
<212> TYPE: DNA
<213> ORGANISM: Artificial Sequence
<220> FEATURE:
<223> OTHER INFORMATION: Synthetic

<400> SEQUENCE: 5
ggatccatga aacccacggt gatcatcacc ggag                                 34
```

<210> SEQ ID NO 6
<211> LENGTH: 36
<212> TYPE: DNA
<213> ORGANISM: Artificial Sequence
<220> FEATURE:
<223> OTHER INFORMATION: Synthetic

<400> SEQUENCE: 6

```
ctcgagctaa accagaccca ctaactttc gcttag                                36
```

<210> SEQ ID NO 7
<211> LENGTH: 966
<212> TYPE: DNA
<213> ORGANISM: Artificial Sequence
<220> FEATURE:
<223> OTHER INFORMATION: Synthetic

<400> SEQUENCE: 7

```
atgagtgatc agccacgccc aacggtcatt attacggctg catcctctgt agtcgtgttg      60
tatgctacca aggccttagc caatcggggc ttgcacgtta taatggccag ccgcaatctt     120
gaaaaagcag agcaagccgc caaaaacttg cagattccgc cggaggccta cacgattttg     180
cacttggact tgtcctcctt ggccagtgtg cgcggctttg ttgaatcatt tcgggcattg     240
aatcgcccct tgcgtgccct tgtctacaat gccgctgtct attatcccct gctcaaggaa     300
cctatctaca gtgtggatgg ctatgaaatc actgtggcca ccaaccattt ggggcatttt     360
cttttgatca acctgctgct agaagacttg aaaaattctc ccgaaagcga taagcgcttg     420
gtgattctcg gcacagtgac agccaaccgc aaagaactcg gcggtaaaat tcccattcct     480 gctcccctg atttgggcaa cctcgaaggc tttgaaaaag gcttcaagaa gccgattgcc     540
atgattaacg gtaagcccct caagtcgggc aaggccttca agacagcat gctcagcaat     600 atgctgacgg cacgggaact gcatcgccgc tttcacgaga gcaccggaat tgtttttaat     660
tccctttacc ccggtggtgt ggccgacaca cccctgtttc gccaccactt ccccctgttt     720
cagaaactct tccccgactt ccagaaaaag attactgggg gctatgtcag ccaagaactg     780
gcgggtgagc gcgtcgcgat ggtggtcgca gacccagagt tcgccagtc gggggtccac     840 tggacctggg gtaatcgcca aaaagaaggc cgcaaagcct tgtccaaga actatcggca     900 gaggcaagtg atgagcaaaa agcccgccgt ctttgggagc tgagtgaaaa actggtggga     960
ttggcc                                                               966
```

<210> SEQ ID NO 8
<211> LENGTH: 38
<212> TYPE: DNA
<213> ORGANISM: Artificial Sequence
<220> FEATURE:
<223> OTHER INFORMATION: Synthetic

<400> SEQUENCE: 8

```
gcaaggcctt caaagacagc atgctcagca atatgctg                             38
```

<210> SEQ ID NO 9
<211> LENGTH: 37
<212> TYPE: DNA
<213> ORGANISM: Artificial Sequence
<220> FEATURE:
<223> OTHER INFORMATION: Synthetic

<400> SEQUENCE: 9

```
                gtctttgaag gccttgcccg acttgaaggg cttaccg                      37

<210> SEQ ID NO 10
<211> LENGTH: 966
<212> TYPE: DNA
<213> ORGANISM: Artificial Sequence
<220> FEATURE:
<223> OTHER INFORMATION: Synthetic

<400> SEQUENCE: 10
atgagtgatc agccacgccc aacggtcatt attacgggtg catcctctgg agtcggattg      60
tatgctacca aggccttagc caatcggggc tggcacgtta atggcctg ccgcaatctt       120 gaaaaagcag agcaagccgc caaaaacttg cagattccgc cggaggccta cacgattttg      180
cacttggact tgtcctcctt ggccagtgtg cgcggctttg ttgaatcatt cgggcattg       240 aatcgcccct tgcgtgccct tgtctgcaat gccgctgtct attatcccct gctcaaggaa      300
cctatctaca gtgtggatgg ctatgaaatc actgtggcca ccaaccattt ggggcatttt      360
cttttgatca acctgctgct agaagacttg aaaaattctc ccgaaagcga taagcgcttg      420
gtgattctcg gcacagtgac agccaaccgc aaagaactcg gcggtaaaat tcccattcct      480
gctccccctg atttgggcaa cctcgaaggc tttgaaaaag cttcaagaa gccgattgcc       540 atgattaacg gtaagcccttt caagtcgggc aaggcctaca agacagcaa gctctgcaat     600 atgctgacgg cacgggaact gcatcgccgc tttcacgaga gcaccggaat tgttttaat      660 tccctttacc ccggttgtgt ggccgacaca ccctgtttc gccaccactt ccccctgttt     720
cagaaactct tccccctctt ccagaaaaag attactgggg gctatgtcag ccaagaactg      780
gcgggtgagc gcgtcgcgat ggtggtcgca gacccagagt ttcgccagtc ggggggtccac    840 tggagctggg gtaatcgcca aaagaaggc cgcaaagcct tgtccaaga actatccggca      900 gaggcaagtg atgagcaaaa agcccgccgt ctttgggagc tgagtgaaaa actggtggga      960
ttggcc                                                                966

<210> SEQ ID NO 11
<211> LENGTH: 322
<212> TYPE: PRT
<213> ORGANISM: Artificial Sequence
<220> FEATURE:
<223> OTHER INFORMATION: Synthetic

<400> SEQUENCE: 11

Met Ser Asp Gln Pro Arg Pro Thr Val Ile Ile Thr Gly Ala Ser Ser
1               5                   10                  15

Gly Val Gly Leu Tyr Ala Thr Lys Ala Leu Ala Asn Arg Gly Trp His
                20                  25                  30

Val Ile Met Ala Cys Arg Asn Leu Glu Lys Ala Glu Gln Ala Ala Lys
            35                  40                  45

Asn Leu Gln Ile Pro Pro Glu Ala Tyr Thr Ile Leu His Leu Asp Leu
        50                  55                  60

Ser Ser Leu Ala Ser Val Arg Gly Phe Val Glu Ser Phe Arg Ala Leu
65                  70                  75                  80

Asn Arg Pro Leu Arg Ala Leu Val Cys Asn Ala Ala Val Tyr Tyr Pro
                85                  90                  95

Leu Leu Lys Glu Pro Ile Tyr Ser Val Asp Gly Tyr Glu Ile Thr Val
                100                 105                 110

Ala Thr Asn His Leu Gly His Phe Leu Leu Ile Asn Leu Leu Leu Glu
            115                 120                 125
```

Asp Leu Lys Asn Ser Pro Glu Ser Asp Lys Arg Leu Val Ile Leu Gly
            130                 135                 140

Thr Val Thr Ala Asn Arg Lys Glu Leu Gly Gly Lys Ile Pro Ile Pro
145                 150                 155                 160

Ala Pro Pro Asp Leu Gly Asn Leu Glu Gly Phe Glu Lys Gly Phe Lys
                165                 170                 175

Lys Pro Ile Ala Met Ile Asn Gly Lys Pro Phe Lys Ser Gly Lys Ala
            180                 185                 190

Tyr Lys Asp Ser Lys Leu Cys Asn Met Leu Thr Ala Arg Glu Leu His
        195                 200                 205

Arg Arg Phe His Glu Ser Thr Gly Ile Val Phe Asn Ser Leu Tyr Pro
210                 215                 220

Gly Cys Val Ala Asp Thr Pro Leu Phe Arg His His Phe Pro Leu Phe
225                 230                 235                 240

Gln Lys Leu Phe Pro Leu Phe Gln Lys Lys Ile Thr Gly Gly Tyr Val
                245                 250                 255

Ser Gln Glu Leu Ala Gly Glu Arg Val Ala Met Val Val Ala Asp Pro
            260                 265                 270

Glu Phe Arg Gln Ser Gly Val His Trp Ser Trp Gly Asn Arg Gln Lys
        275                 280                 285

Glu Gly Arg Lys Ala Phe Val Gln Glu Leu Ser Ala Glu Ala Ser Asp
290                 295                 300

Glu Gln Lys Ala Arg Arg Leu Trp Glu Leu Ser Glu Lys Leu Val Gly
305                 310                 315                 320

Leu Ala

<210> SEQ ID NO 12
<211> LENGTH: 322
<212> TYPE: PRT
<213> ORGANISM: Artificial Sequence
<220> FEATURE:
<223> OTHER INFORMATION: Synthetic

<400> SEQUENCE: 12

Met Ser Asp Gln Pro Arg Pro Thr Val Ile Ile Thr Gly Ala Ser Ser
1               5                   10                  15

Gly Val Gly Leu Tyr Ala Thr Lys Ala Leu Ala Asn Arg Gly Trp His
            20                  25                  30

Val Ile Met Ala Cys Arg Asn Leu Glu Lys Ala Glu Gln Ala Ala Lys
        35                  40                  45

Asn Leu Gln Ile Pro Pro Glu Ala Tyr Thr Ile Leu His Leu Asp Leu
    50                  55                  60

Ser Ser Leu Ala Ser Val Arg Gly Phe Val Glu Ser Phe Arg Ala Leu
65                  70                  75                  80

Asn Arg Pro Leu Arg Ala Leu Val Cys Asn Ala Ala Val Tyr Tyr Pro
                85                  90                  95

Leu Leu Lys Glu Pro Ile Tyr Ser Val Asp Gly Tyr Glu Ile Thr Val
            100                 105                 110

Ala Thr Asn His Leu Gly His Phe Leu Leu Ile Asn Leu Leu Leu Glu
        115                 120                 125

Asp Leu Lys Asn Ser Pro Glu Ser Asp Lys Arg Leu Val Ile Leu Gly
    130                 135                 140

Thr Val Thr Ala Asn Arg Lys Glu Leu Gly Gly Lys Ile Pro Ile Pro
145                 150                 155                 160

Ala Pro Pro Asp Leu Gly Asn Leu Glu Gly Phe Glu Lys Gly Phe Lys
            165                 170                 175

Lys Pro Ile Ala Met Ile Asn Gly Lys Pro Phe Lys Ser Gly Lys Ala
        180                 185                 190

Phe Lys Asp Ser Lys Leu Cys Asn Met Leu Thr Ala Arg Glu Leu His
    195                 200                 205

Arg Arg Phe His Glu Ser Thr Gly Ile Val Phe Asn Ser Leu Tyr Pro
210                 215                 220

Gly Cys Val Ala Asp Thr Pro Leu Phe Arg His His Phe Pro Leu Phe
225                 230                 235                 240

Gln Lys Leu Phe Pro Leu Phe Gln Lys Lys Ile Thr Gly Gly Tyr Val
                245                 250                 255

Ser Gln Glu Leu Ala Gly Glu Arg Val Ala Met Val Val Ala Asp Pro
            260                 265                 270

Glu Phe Arg Gln Ser Gly Val His Trp Ser Trp Gly Asn Arg Gln Lys
        275                 280                 285

Glu Gly Arg Lys Ala Phe Val Gln Glu Leu Ser Ala Glu Ala Ser Asp
    290                 295                 300

Glu Gln Lys Ala Arg Arg Leu Trp Glu Leu Ser Glu Lys Leu Val Gly
305                 310                 315                 320

Leu Ala

<210> SEQ ID NO 13
<211> LENGTH: 320
<212> TYPE: PRT
<213> ORGANISM: Artificial Sequence
<220> FEATURE:
<223> OTHER INFORMATION: Synthetic

<400> SEQUENCE: 13

Met Glu Gln Pro Met Lys Pro Thr Val Ile Ile Thr Gly Ala Ser Ser
1               5                   10                  15

Gly Val Gly Leu Tyr Gly Ala Lys Ala Leu Ile Asp Lys Gly Trp His
            20                  25                  30

Val Ile Met Ala Cys Met Leu Asp Lys Thr Gln Lys Val Ala Asp Glu
        35                  40                  45

Leu Gly Phe Pro Lys Asp Ser Tyr Thr Ile Ile Lys Leu Asp Leu Gly
    50                  55                  60

Tyr Leu Asp Ser Val Arg Arg Phe Val Ala Gln Phe Arg Glu Leu Gly
65                  70                  75                  80

Arg Pro Leu Lys Ala Leu Val Cys Asn Ala Ala Val Tyr Phe Pro Leu
                85                  90                  95

Leu Asp Glu Pro Leu Trp Ser Ala Asp Asp Tyr Glu Leu Ser Val Ala
            100                 105                 110

Thr Asn His Leu Gly His Phe Leu Leu Cys Asn Ile Leu Leu Glu Asp
        115                 120                 125

Leu Lys Ala Cys Pro Asp Ala Asp Lys Arg Leu Ile Ile Leu Gly Thr
    130                 135                 140

Val Thr Ala Asn Ser Lys Glu Leu Gly Gly Lys Ile Pro Ile Pro Ala
145                 150                 155                 160

Pro Pro Asp Leu Gly Asn Phe Glu Gly Phe Glu Ala Gly Phe Lys Lys
                165                 170                 175

Pro Ile Ala Met Ile Asn Asn Lys Lys Phe Lys Ser Gly Lys Ala Tyr
            180                 185                 190

Lys Asp Ser Lys Leu Cys Asn Met Leu Thr Thr Arg Glu Leu His Arg

-continued

```
            195                 200                 205
Arg Phe His Gln Glu Thr Gly Ile Val Phe Asn Ser Leu Tyr Pro Gly
    210                 215                 220

Cys Val Ala Asp Thr Pro Leu Phe Met His Tyr Ser Leu Phe Arg Thr
225                 230                 235                 240

Ile Phe Pro Trp Phe Gln Lys Asn Val Thr Lys Gly Tyr Val Ser Gln
                245                 250                 255

Glu Leu Ala Gly Glu Arg Val Ala Met Val Val Ala Asp Asp Lys Phe
                260                 265                 270

Lys Asp Ser Gly Val His Trp Ser Trp Gly Asn Arg Gln Gln Ala Gly
                275                 280                 285

Arg Glu Ala Phe Val Gln Glu Leu Ser Glu Gln Gly Ser Asp Ala Gln
                290                 295                 300

Lys Ala Gln Arg Met Trp Asp Leu Ser Glu Lys Leu Val Gly Leu Val
305                 310                 315                 320
```